US007910123B2

(12) United States Patent
McKay

(10) Patent No.: US 7,910,123 B2
(45) Date of Patent: Mar. 22, 2011

(54) METHODS OF TREATING A TRAUMA OR DISORDER OF THE KNEE JOINT BY LOCAL ADMINISTRATION AND SUSTAINED-DELIVERY OF A BIOLOGICAL AGENT

(75) Inventor: William F. McKay, Memphis, TN (US)

(73) Assignee: Warsaw Orthopedic IN (US)

( * ) Notice: Subject to any disclaimer, the term of this patent is extended or adjusted under 35 U.S.C. 154(b) by 0 days.

(21) Appl. No.: 11/850,183

(22) Filed: Sep. 5, 2007

(65) Prior Publication Data
US 2009/0060971 A1   Mar. 5, 2009

(51) Int. Cl.
*A61F 2/02*      (2006.01)
*A61K 38/16*   (2006.01)
*A61K 38/20*   (2006.01)
*A61M 31/00*  (2006.01)
*A61P 21/00*   (2006.01)

(52) U.S. Cl. ....... 424/423; 128/898; 424/422; 424/85.2; 604/502

(58) Field of Classification Search .......................... None
See application file for complete search history.

(56) References Cited

U.S. PATENT DOCUMENTS

| | | | |
|---|---|---|---|
| 2,568,207 A | 9/1951 | Spicher | |
| 4,353,370 A | 10/1982 | Evans | |
| 4,532,926 A | 8/1985 | O'Holla | |
| 4,534,350 A | 8/1985 | Golden et al. | |
| 5,378,475 A | 1/1995 | Smith et al. | |
| 5,423,858 A | 6/1995 | Bolanos et al. | |
| 5,545,180 A | 8/1996 | Le et al. | |
| 5,773,019 A | 6/1998 | Ashton et al. | |
| 6,001,386 A | 12/1999 | Ashton et al. | |
| 6,083,522 A * | 7/2000 | Chu et al. ...................... | 424/423 |
| 6,656,182 B1 | 12/2003 | Hayhurst | |
| 6,916,483 B2 | 7/2005 | Ralph et al. | |
| 6,936,270 B2 | 8/2005 | Watson et al. | |
| 2001/0010005 A1 | 7/2001 | Kammerer et al. | |

(Continued)

FOREIGN PATENT DOCUMENTS

WO        WO99/24061 A1      5/1999

(Continued)

OTHER PUBLICATIONS

Image—Google.com_lipscombclinic.com_knee anatomy publication (URL on image), last accessed Feb. 19, 2009.*

(Continued)

*Primary Examiner* — Cherie M Woodward

(57) ABSTRACT

Methods and apparatus of providing a subject with postoperative, sustained-release of a biological agent within a synovial joint is disclosed. These methods involve securing a depot containing the biological agent to a ligament, tendon, muscle within the joint to provide sustained-release of the agent while allowing for normal joint articulation. This methodology may be utilized to provide for sustained-release of a biological agent useful in treating various traumas and disorders of the joint. Such biological agents include antagonists of inflammation-related proteins, such as TNF-α, IL-1β, IL-6, IL-8, NF-κB, High Mobility Group Box 1 (HMG-B1), IL-2, IL-15 and steroidal and non-steroidal anti-inflammatories. Other biological agents include anti-inflammatory cytokines such as IL-10, IL-4, IL-13, and TGF-β. The biological agents also include osteogenic and cartilage producing growth factors such as, but not limited to, BMP-2, BMP-4, BMP-6, BMP-7, BMP-8, and MIA CD-RAP. Finally, the biological agents include siRNA and/or therapeutic antibodies.

17 Claims, 5 Drawing Sheets

U.S. PATENT DOCUMENTS

| | | |
|---|---|---|
| 2002/0169162 A1 | 11/2002 | Smith et al. |
| 2003/0195527 A1 | 10/2003 | Helmus |
| 2004/0115236 A1 | 6/2004 | Chan et al. |
| 2005/0025765 A1 | 2/2005 | DiMauro et al. |
| 2005/0031665 A1 | 2/2005 | Watson et al. |
| 2005/0152949 A1* | 7/2005 | Hotchkiss et al. ............ 424/423 |
| 2005/0260247 A1 | 11/2005 | Ralph et al. |
| 2006/0195139 A1 | 8/2006 | Gertner |
| 2006/0246103 A1 | 11/2006 | Ralph et al. |
| 2008/0228193 A1 | 9/2008 | Matityahu |

FOREIGN PATENT DOCUMENTS

| | | |
|---|---|---|
| WO | WO02/28366 A2 | 4/2002 |
| WO | 2004012627 A1 | 2/2004 |
| WO | WO2006/028939 A1 | 3/2006 |
| WO | 2007121288 A2 | 10/2007 |
| WO | 2008112592 A1 | 9/2008 |

OTHER PUBLICATIONS

Steadman's Medical Dictionary, 27th Edition, 2000, definition of Cartilage.*

Steadman's Medical Dictionary, 27th Edition, 2000, definition of Ligament.*

Eaton, et al., (Med Health R.I. Jul. 2004;87(7):201-4, Abstract Only).*

International Search Report in PCT/US2008/075435, filed Sep. 5, 2008, 9 pages.

* cited by examiner

METHODS OF TREATING A TRAUMA OR DISORDER OF THE KNEE JOINT BY LOCAL ADMINISTRATION AND SUSTAINED-DELIVERY OF A BIOLOGICAL AGENT

FIELD OF THE INVENTION

The present invention relates to methods of treating a trauma or disorder of a joint comprising delivery of a biological agent to the joint as a depot implant while also providing for normal articulation of the joint. Embodiments of the methods of the present invention include minimally invasive or surgical attachment of a pharmaceutical depot implant containing a biological agent to a ligament of a joint such as, but not limited to, a knee joint. The methods of the present invention may be utilized to treat pain and inflammation associated with the cartilage, subchondral bone, ligament, tendon and/or muscle of the joint. These methods are also contemplated for the prophylactic or therapeutic treatment of various traumas or disorders of the knee joint, including but not limited to primary repair or reconstruction of the anterior or posterior cruciate ligament, the medial or lateral collateral ligament, the patellar ligament, or disorders such as osteoarthritis and rheumatoid arthritis.

BACKGROUND OF THE INVENTION

There exist numerous components which must work in tandem in order to provide maximum stability and mobility to joints, especially the knee joint which, under even normal conditions, sustains a load of approximately 2-7 times the body weight of the subject. Referring to the knee joint as an example of a synovial joint, the quadriceps (front of the thigh area) and hamstrings (back of the thigh area) are the two groups of muscles that control the knee joint. Referring to FIG. 1, the three bones that form the knee joint 1 are the femur 5 (thigh bone), patella (knee cap) and tibia 10 (shinbone). The tibia resides next to the fibula 15, which begins just below the knee joint 1 and runs down the leg to the ankle. The knee joint 1 includes the articular cartilage of the adjacent bones, an inner synovial membrane (synovium), a joint capsule, along with synovial fluid within the joint space. The bones of the knee joint 1 are held in place by a number of primary and secondary ligaments. The primary ligaments being the medial collateral ligament 20 (MCL; connecting the femur to the tibia on the inside of the knee joint), the lateral collateral ligament 25 (LCL; connecting the femur to the fibula on the outside of the knee), the anterior cruciate ligament 35 (ACL; connecting the femur to the tibia deep within the center of the knee joint space), the posterior cruciate ligament 30 (PCL; also located deep within the knee, and as with the ACL, also connecting the femur and tibia), and the patellar ligament (connecting the patella to the tibia). The bones of the knee joint 1 are lined with articular cartilage, which absorbs shock, protects these bones, and allows the knee to move in a fluid motion. Additional cartilage is found in the form of the medial meniscus 40 and lateral meniscus 45. Both menisci are comprised of a fibrous cartilage and are located on each side of the knee on the top of the tibial plateau, absorbing the shear forces associated with normal stress associate with the knee joint.

There are a plethora of joint traumas or acute or chronic disorders associated with the synovial joints which require therapeutic intervention. Often times such traumas and disorders coincide with a substantial inflammatory response and/or persistent pain radiating from the joint area. Thus, inflammation can be an acute response to trauma or a chronic response to the presence of inflammatory agents brought about by any number of processes or events which trigger tissue damage within the knee joint. For example, when tissues are damaged, TNF-a attaches to cells to cause them to release other cytokines that cause inflammation. One type of recruited immune system cell is the macrophage. Macrophages release interleukin-1 beta ("IL-β") and tumor necrosis factor-alpha ("TNF-a"), pro-inflammatory cytokines heavily involved in orchestrating the immediate and local physiological effects of injury or infection. For instance, once released, pro-inflammatory cytokines promote inflammation. The purpose of the inflammatory cascade is to promote healing of the damaged tissue, but once the tissue is healed the inflammatory process does not necessarily end. Left unchecked, this can lead to degradation of surrounding tissues and associated chronic pain. Thus, pain can become a disease state in itself. That is, when this pathway is activated, inflammation and pain ensue. Cycles of inflammation and associated pain often times set in. There are numerous examples of conditions in which this cycle is present including, but not limited to, conditions related to a trauma or acute or chronic disorder associated with the knee joint.

As noted above, and as an example, TNF-a inhibitors have been developed for therapeutic use to treat a knee joint trauma or disorder, such as rheumatoid arthritis and osteoarthritis. TNF-a inhibitors currently in use are generally administered systemically via intravenous infusion and subcutaneous injection, but there are side effects of anti-TNF therapies associated with the higher doses and systemic administration that are common with these therapies. In the case of direct injection, a bolus of the pharmaceutical agent is injected as near to the target site as placement of a needle will allow. Unfortunately, it provides a limited quantity of agent that must move through the tissue to the target site. Such methods are inadequate to serve the needs of patients. Anti-TNF therapy is generally needed over an extended period of time, so repeated injections are likely to be necessary. Injection site pain and reactions sometimes develop with anti-TNF-a agents. What is needed is a system and method for controlled and directed delivery of a biological agent, such as TNF-a inhibitors, for the treatment and prevention of inflammation and pain, capable of being delivered for an extended period of time at, or in close proximity to, a targeted site such as the site of trauma or inflammation.

Despite current knowledge in the field covering the surgical and non-surgical treatment of inflammation, traumas and/or disorders of joints, there remains a need for improved methods of treating acute and chronic inflammation and/or pain associated with recovery from, treatment or prevention of these disorders. The methods of the present invention address and meet these needs by disclosing methods of treating inflammation and/or pain associated with, but not limited to, the knee joint. These methods include minimally invasively or surgically delivering and tethering pharmaceutical depot implant containing a formulated biological agent within the knee joint, or any joint for that matter, so as to provide for sustained-release of the respective biological agent while maintaining normal joint articulation, thus maximizing pain relief and prospects of recovery for the subject.

SUMMARY OF THE INVENTION

The present invention relates to a method of providing a subject with sustained-release of a biological agent within a joint such as, but not limited to, the knee joint. This method involves minimally invasively or surgically attaching a pharmaceutical depot implant containing the biological agent to a ligament, tendon, muscle or other structure within the joint so as to provide sustained-release of the agent to treat inflammation, a trauma, and/or disorder in the joint, while allowing for normal joint articulation.

The present invention relates, in part, to methods of minimally invasively or surgically attaching a pharmaceutical depot implant to the anterior cruciate ligament (ACL), or an allograft thereof, in order to promote sustained-release of a biological agent within the knee joint of the subject. In one embodiment of the invention, the depot may be minimally invasively attached to the ACL during an arthroscopy procedure to repair or reconstruct a torn ACL. In another embodiment of the invention, the depot may be minimally invasive or surgically attached to the ACL within the knee joint addressing any other trauma or knee disorder. In yet another embodiment of the invention, the depot may be minimally invasively or surgically attached to the ACL in order to provide either therapeutic or prophylactic relief from a trauma or knee disorder which previously was not addressed by surgical intervention.

The present invention also relates to methods of minimally invasively or surgically attaching a pharmaceutical depot implant to the posterior cruciate ligament (PCL), or an allograft thereof, in order to promote sustained-release of a biological agent within the knee joint of the subject. In one embodiment of the invention, the depot may be minimally invasively attached to the PCL during an arthroscopy procedure to repair or reconstruct a torn PCL. In another embodiment of the invention, the depot may be surgically attached to the PCL during a surgical procedure within the knee joint addressing any other trauma or knee disorder. In yet another embodiment of this invention, the depot may be minimally invasively or surgically attached to the PCL in order to provide either therapeutic or prophylactic relief from a trauma or knee disorder which previously was not addressed by surgical intervention.

The present invention also relates to methods wherein multiple pharmaceutical depot implants may be minimally invasively or surgically secured to both the anterior cruciate ligament and the posterior cruciate ligament, thus promoting the prolonged prophylactic or therapeutic effects contemplated herein.

The present invention further relates to sustained-release of a biological agent within the synovial space of the knee to promote prophylactic or therapeutic indications contemplated herein. One embodiment of this portion of the invention relates to attachment of the depot to the patellar ligament, or an allograft thereof, providing for a central location within the knee joint so as to release the biological agent within the synovial joint space as well as being in a location that will not interfere with normal joint articulation. Attachment of the sustained-release depot to the patellar ligament is contemplated to provide post-operative therapy covering a minimally invasive or surgical procedure to the patellar ligament, a minimally invasive or surgical procedure within the knee joint addressing any other trauma or knee disorder, or to provide either therapeutic or prophylactic relief from a trauma or knee disorder which on its own does not call for surgical intervention.

Another embodiment of the present invention relates to attachment of the depot to either or both the medial collateral ligament and/or the lateral collateral ligament, or an allograft thereof in a location that will not interfere with normal joint articulation. Attachment of the sustained-release depot to either collateral ligament is contemplated to provide sustained-release therapy to either or both collateral ligaments, a minimally invasive or surgical procedure within the knee joint addressing any other trauma or knee disorder, or to provide either therapeutic or prophylactic relief from a trauma or knee disorder which on its own does not call for surgical intervention.

The present invention also relates to methods wherein multiple pharmaceutical depot implants may be minimally invasively or surgically secured to the anterior cruciate ligament, the posterior cruciate ligament, the patellar ligament, the medial collateral ligament, and/or the lateral collateral ligament, or any combination thereof, so as to afford maximum therapeutic or prophylactic effect from the sustained-release of a biological agent from the respective depot implant(s).

In one embodiment, the injury or disorder is associated with an intraarticular ligament (e.g., the ACL and PCL). In another embodiment the trauma or disorder effects other ligaments of the knee joint (including but not limited to the lateral or medial collateral ligaments, as well as the patellar ligament). In other embodiments, the injuries or disorders relate to problems associated with the articular cartilage, such as osteoarthritis, chondromalacia, and rheumatoid arthritis. Another embodiment relates to treating meniscal injuries, such as meniscal tears. Additional embodiments include, but are not limited to, chondral fractures, traumas or injuries associated with the patella, just to name a few. Thus, the methods of the present invention may be utilized to deliver a biological agent to the knee joint area in a prolonged, sustained time frame and provide therapeutic or prophylactic treatment of any trauma or disorder of the knee while allowing for normal articulation of the knee joint.

The biological agent(s) used in the methods of the present invention may be any molecule, cell, or physical stimulus which provides therapeutic or prophylactic relief for acute or chronic pain and/or inflammation associated with any knee trauma or knee disorder, including traumas associated with the cartilage, subchondral bone, tendons, ligaments and muscles in and around the knee joint. The biological agent includes, but is not limited to, an anti-inflammatory agent, an antibiotic and/or an analgesic, or combinations thereof, each of which may be presented in a sustained-release formulation as a pharmaceutical depot implant or depot injection. Such anti-inflammatory agents may be in any form such that administration of the entity promotes the desired anti-inflammatory response, including any molecule, cell or physical stimulus which positively effects the activity of an anti-inflammatory response. As discussed herein, a targeted inflammatory cytokine or protein related to the inflammatory response includes, but is not limited to, TNF-$\alpha$, IL-1$\beta$, IL-6, IL-8, NF-$\kappa$B, High Mobility Group Box 1 (HMG-B1), IL-2, IL-15 and MMPs, while a specific anti-inflammatory cytokine or related protein which may promote an anti-inflammatory response includes but is not limited to IL-10, IL-4, IL-13 and TGF-$\beta$, as well as any other cytokine or pathway related protein which modulates the respective anti-inflammatory cytokine so as to impart an increase in the ability of reduce patient inflammation and pain within the synovial joint. Additionally, the biological agents(s) may be comprised of an analgesic, an antibiotic, a steroidal anti-inflammatory, and/or a non-steriodal anti-inflammatory. Additionally, such agents may include a small molecule, an oligonucleotide, an antibody or relevant fragment, siRNA, as well as any factor in the form of a molecule cell or physical stimulus which regulates expression of a gene of interest or affects stability or activity of expression and/or translation of a protein, so as to modulate the target so as to provide a level of relief to the joint. Accordingly, the sustained-release of the contemplated biological agent(s) after the implantation of the depot in a ligament of the synovial joint will result in local, biologically effective concentrations of the biological agent(s) in or around the inflamed or infected joint over a period of time.

One embodiment of the methods of the present invention is to utilize a drug delivery device which is pharmaceutical depot implant. As discussed throughout this specification, a pharmaceutical depot implant may be inserted within the knee joint, such as being secured to a cruciate, collateral and/or patellar ligament by surgical or non-surgical minimally invasive techniques. Surgical techniques for securing the depot implant to the target ligament, tendon or muscle will include any suturing technique available to the skilled artisan, the use of any suture-anchor apparatus, injecting the depot into a ligament, or any other art accepted method of surgically attaching the depot implant to the target ligament, tendon or muscle. The implantation of such a device will be in such a manner as to allow for normal joint articulation in the post-operative setting while also acting as an adequate reservoir for the prolonged release of the biological agent(s) during the prescribed rehabilitation period. The drug delivery device will be capable of carrying the drug formulation in such quantities as therapeutically or prophylactically required for treatment over the pre-selected period. The device may also provide protection to the formulation from degradation by body processes (such as proteases) for the duration of treatment. The sustained-release of the contemplated biological agent(s) and any additional active ingredient, carrier or excipient will result in local, biologically effective concentrations of the biological agent(s) in or around the damaged cartilage, subchondral bone, ligament, tendon, or muscle in the vicinity of the patellar ligament, which may act as a point of attachment for the depot implant. Another embodiment of the methods presented herein represents delivery of a sustained-release formulation as a repository or depot injection. Carriers suitable for sustained-release depot formulations include, but are not limited to, microspheres, films, capsules, particles, gels, coatings, matrices, wafers, pills or other pharmaceutical delivery compositions.

An object of the present invention relates to the use of the sustained-delivery devices to treat joint inflammation, trauma, and/or a disorder, where parenteral administration of such a device is accomplished while maintaining normal articulation of the knee joint.

An object of the present invention relates to the use of sustained-delivery devices to treat a knee trauma and/or disorder, where parenteral administration of such a device is accomplished while maintaining normal articulation of the knee joint.

Another object of the present invention relates to sustained-delivery of a biological agent from an implanted dosage to provide an effective and inexpensive method of providing prophylactic care to such populations including, but not limited to, situations whereby a biological agent is delivered to either prevent the onset of osteoarthritis or provide therapeutic intervention in order to positively modulate osteoarthritis.

Another object of the present invention is to provide for sustained-delivery of a biological agent from an implanted drug delivery device within a synovial joint such that the drug treats joint inflammation, trauma and/or a disorder. Accordingly, the use of the device obviates the need for regular dosing by the patient and increases patient compliance with either a prescribed therapeutic regimen or a prophylactic regimen prescribed prior to the onset of symptoms.

Another object of the present invention is to provide for sustained-delivery of a biological agent from an implanted drug delivery device within the knee joint such that the drug treats a knee trauma or knee disorder. Accordingly, the use of the device obviates the need for regular dosing by the patient and increases patient compliance with either a prescribed therapeutic regimen or a prophylactic regimen prescribed prior to the onset of symptoms.

The term "biological agent" also refers to any molecule, cell, or physical stimulus which would be contemplated for administration to the joint space of a subject, including a knee joint, in order to promote rehabilitation following minimally invasive or surgical intervention to treat cartilage, subchondral bone, ligament, tendon, muscle damage, or to provide prophylactic or therapeutic treatment of a trauma or disorder of the joint. Such examples would include, but are not limited to NSAIDS, antibiotics, analgesics, and the like, as well as any molecule, cell, or physical stimulus which decreases, blocks, inhibits, abrogates or interferes with the pro-inflammatory cascade of proteins leading to an inflammatory response. For example, a suitable TNF-a antagonist can bind TNF-a, and includes anti-TNF-a antibodies and/or receptor molecules which bind specifically to TNF-a, as well as small molecules which antagonize TNF-a activity. A suitable TNF-a antagonist can also prevent or inhibit TNF-a synthesis and/or TNF-a release. Another example may also provide for any cytokine or biologically active fragment thereof which possesses the ability to decrease, block, inhibit, abrogate or interfere with the pro-inflammatory response promoted by other cytokine proteins (e.g., IL-10, IL-4, IL-13 and TGF-β) as well as any molecule, cell, or physical stimulus which positively modulates the anti-inflammatory effect of such an anti-inflammatory cytokine so as to impart an increase in the ability to reduce patient inflammation and pain.

The term "pro-inflammatory" shall mean an endotoxin or any other molecule, cell or physical stimuli that initiates monocytes and macrophages to secrete cytokines which lead to an inflammatory response, such as, for example, TNF-a.

As used herein, the term "sustained-release" refers to the release of an anti-cytokine agent, anti-inflammatory cytokine and/or other molecule, cell or physical stimulus, as described herein, from microparticles over a defined period of time in a continuous, discontinuous, linear or nonlinear manner, such as a biphasic release (i.e., an initial burst of release of the active ingredient(s) followed by continuous release of the active ingredient(s) from microparticle over time).

The terms "effective amount" or "pharmaceutically effective amount," as provided herein, refer to a nontoxic but sufficient amount of the active ingredient in order to provide the desired biological result. That result can be reduction and/or alleviation of the pain and/or inflammation associated with either a knee trauma or knee disorder. An appropriate "effective amount" in any individual case may be determined by one of ordinary skill in the art using routine experimentation.

The terms "pharmaceutically acceptable" or "pharmacologically acceptable" mean a material may be administered to an individual in a drug delivery device along with the formulated biological agent without causing any undesirable biological effects or interacting in a deleterious manner with any of the components of the composition in which it is contained.

The term "subject" or "patient" or "vertebrate subject" or "vertebrate patient" is meant any member of the Phylum Chordata, including, without limitation, humans and other primates, including nonhuman primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In the case of treating a knee trauma or disorder, "preventing" or "prevention" may also occur in a situation where a course of treatment is advanced in order to prevent a recurrence of a previous acute episode. In addition, "treating" or "treatment" does not require complete alleviation of signs or symptoms, does not require a cure, and specifically includes protocols which have only a marginal effect on the subject.

As used herein, "modulating" ranges from initiating to shutting down, and within that range is included enhancing significantly or slightly to inhibiting significantly or slightly. The term "inhibiting" includes a down-regulation which may reduce or eliminate the targeted function, such as the production of a protein or the translation of an oligonucleotide sequence. For example, a given patient's condition may require only inhibition of a single molecule, such as TNF, or modulating more than one molecule in a cascade of upstream and/or downstream events in the pathway.

The term "microparticle" as used herein, refers to a particle of about 100 nm to about 150 μm in diameter, with the majority of applications utilizing microparticles in the range from about 500 nm to about 10 μm in diameter, and at least a population of microspheres in a diameter permitting parenteral administration. A microparticle for use in delivering the anti-cytokine, anti-inflammatory cytokine and/or related active ingredients of the present invention will be sterilizable, non-toxic and preferably biodegradable. As noted elsewhere herein, such materials include, without limitation, poly(α-hydroxy acid), polyhydroxybutyric acid, polycaprolactone, polyorthoester, polyanhydride, polyvinyl alcohol and ethylenevinyl acetate. As noted in additional detail herein, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the desired dose of the active ingredient(s).

The phrase "minimally invasive" as used herein, refers to non-operative means of incorporating a pharmaceutical depot into a joint. For example, the depot may be implanted non-operatively in that the patient is under anesthesia local to the joint and the depot is implanted through a cannula. The definition of minimally invasive is not limited to this embodiment and may include any non-operative or outpatient procedure understood in the art.

DETAILED DESCRIPTION OF THE INVENTION

Figure 1:
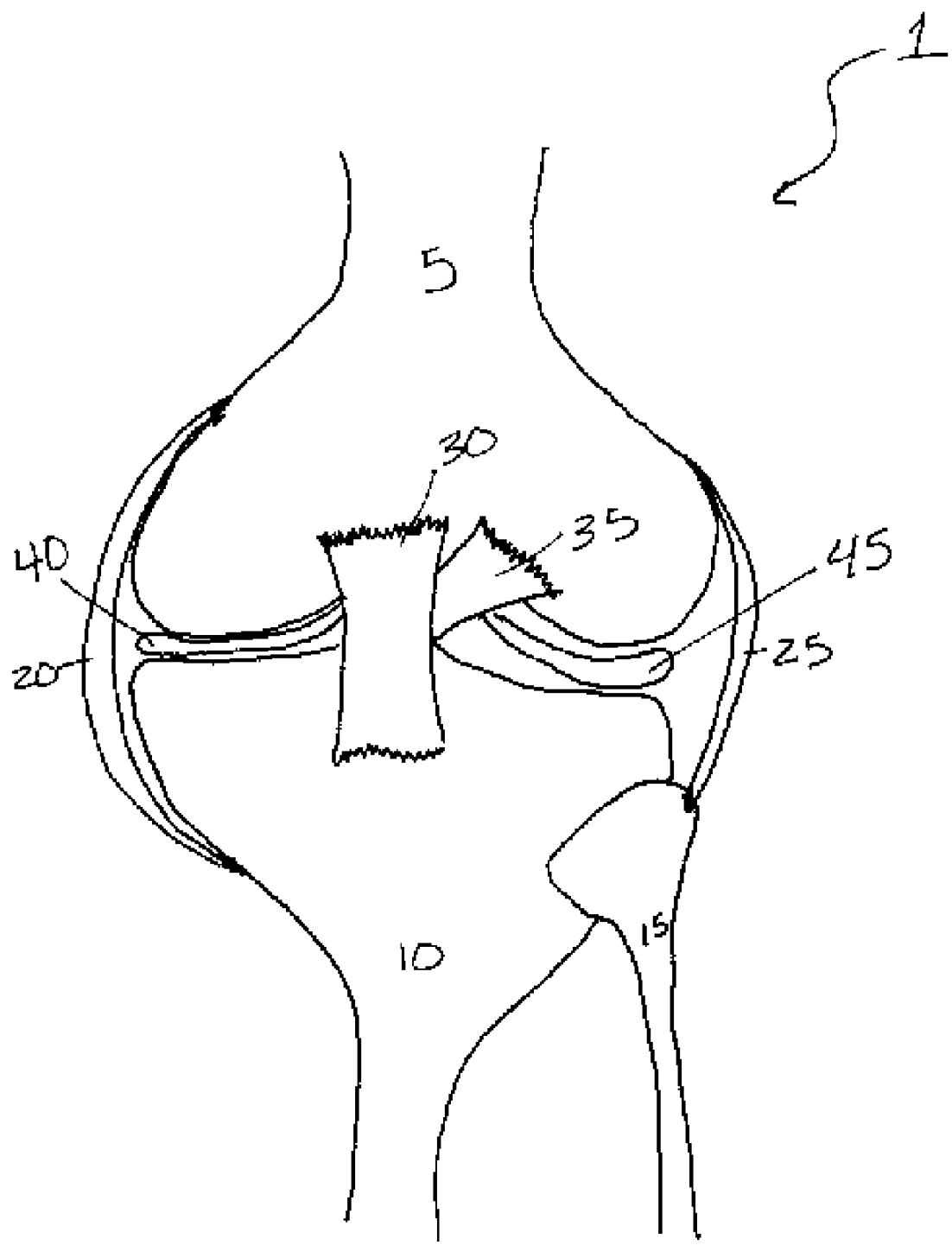
FIG. 1 illustrates a rear view of a right knee joint.

For the purposes of promoting and understanding the principles of the invention, reference will now be made to numerous embodiments and specific language will be used to describe the same. More specifically, the reference will be made to an embodiment of the invention that is targeted toward treating the knee joint. However, the invention is not limited to a knee joint and may be applicable, but not limited, to a hip joint, a shoulder joint, an elbow joint, or any synovial joint, being contemplated as would normally occur to one skilled in the art to which the invention relates. Accordingly, it should be understood that no limitation of the scope of the invention to a knee joint is thereby intended by the embodiments below.

The present invention relates to methods and systems for providing therapeutic or prophylactic treatment within a joint space which comprises administering to a target site within a joint space of a subject in need of treatment a pharmaceutically effective amount of a pharmaceutical composition comprising one or more biological agents, wherein the agent(s) are administered by a sustained-release depot implant or depot injection. Thus, administration of the biological agent is localized to a specific region of the joint space and release of the biological agent(s) within the joint space is controlled over time. The depot implant or depot injection is administered such that the subject will experience acceptable post-procedure joint articulation. Thus, in one embodiment of the present invention, the biological agent includes, but is not limited to, an anti-inflammatory agent, antibiotic, analgesic, or any combination thereof that may be presented in a sustained-release formulation such as a depot implant or depot injection. In another embodiment of the methods of the present invention the depot implant is a biological depot implant. As discussed throughout this specification, a pharmaceutical depot implant may be inserted within the knee joint, such as being secured to a cruciate, patellar and/or collateral ligament by surgical or non-surgical techniques. The implantation of such a device will be in such a manner as to allow for normal joint articulation post-administration while acting as an adequate reservoir for the prolonged release of the biological agent(s) during the rehabilitation period. The drug delivery device will be capable of carrying the drug formulation in such quantities as therapeutically or prophylactically required for treatment over the pre-selected period. The device may also provide protection to the formulation from degradation by body processes (such as proteases) for the duration of treatment. The sustained-release of the contemplated biological agent(s) and any additional active ingredient, carrier or excipient will result in local, biologically effective concentrations of the biological agent(s) in or around a damaged cartilage, subchondral bone, ligament, tendon or muscle which may act as a point of attachment for the depot implant. Another embodiment of the methods presented herein represents delivery of a sustained-release formulation as a repository or depot injection. Carriers suitable for the sustained-release depot formulations include, but are not limited to, rods, microspheres, films, capsules, particles, gels, coatings, matrices, wafers, pills or other pharmaceutical delivery compositions.

The present invention further relates to methods and systems of providing a subject with a sustained-release of a biological agent within a joint in order to treat or prevent pain, inflammation, or other condition associated with a trauma or disorder of the joint. These methods involve minimally invasively or surgically attaching a pharmaceutical depot implant containing the biological agent to a ligament, tendon, muscle or other structure within the joint so as to provide for sustained-release of a biological agent(s) while also promoting normal joint articulation in the post-operative setting.

The present invention relates, in part, to methods of minimally invasively or surgically attaching a pharmaceutical depot implant to the anterior cruciate ligament (ACL), or an allograft thereof, in order to promote post-operative, sustained-release of a biological agent within the knee joint of the subject. In one embodiment of the invention, the depot may be minimally invasively attached to the ACL during an arthroscopy procedure to repair or reconstruct a torn ACL. In a further embodiment, the depot may be attached to the ACL distal to the PCL such that the depot will not interfere with the PCL. In another embodiment of the invention, the depot may be surgically attached to the ACL during a surgical procedure within the knee joint addressing any other knee trauma or disorder. In yet another embodiment of the invention, the depot may be minimally invasively or surgically attached to the ACL in order to provide either therapeutic or prophylactic relief from a knee trauma or disorder which previously was not addressed by surgical intervention.

The present invention also relates in part to methods of minimally invasively or surgically attaching a pharmaceutical depot implant to the posterior cruciate ligament (PCL) in order to promote sustained-release of a biological agent within the knee joint of the subject. In one embodiment of the invention, the depot may be minimally invasively attached to the PCL during an arthroscopy procedure to repair or reconstruct a torn PCL. In a further embodiment, the depot may be attached to the PCL distal to the ACL such that the depot will not interfere with the ACL. In another embodiment of the invention, the depot may be surgically attached to the PCL during a surgical procedure within the knee joint addressing any other trauma or knee disorder. In yet another embodiment of the invention, the depot may be minimally invasively or surgically attached to the PCL in order to provide either therapeutic or prophylactic relief from a trauma or knee disorder which previously was not addressed by surgical intervention.

The present invention also relates to methods wherein multiple pharmaceutical depot implants may be minimally invasively or surgically secured to the anterior cruciate ligament and the posterior cruciate ligament, thus promoting the prolonged prophylactic or therapeutic effects contemplated herein.

The present invention further relates to sustained-release of a biological agent within the synovial space of the knee to promote prophylactic or therapeutic indications contemplated herein. One embodiment of this portion of the invention relates to attachment of the depot to the patellar ligament, providing for a central location within the knee joint so as to release the biological agent within the synovial joint space as well as being in a location that allows for normal joint articulation during the post-operative recovery period.

A further embodiment of the present invention relates to attachment of the depot to either or both the medial collateral ligament and/or the lateral collateral ligament, or an allograft thereof in a location that will not interfere with normal joint articulation. In one embodiment, the depot may be secured within the synovial space of the knee and distal to the joint capsule membrane. Attachment of the sustained-release depot to either collateral ligament is contemplated to provide sustained-release therapy covering a minimally invasively or surgical procedure to the collateral ligaments, a minimally invasively or surgical procedure within the knee joint addressing any other trauma or knee disorder, or to provide either therapeutic or prophylactic relief from a trauma or knee disorder which on its own does not call for surgical intervention.

Attachment of the sustained-release depot implant to the cruciate, patellar and/or collateral ligaments, individually or in any combination, are contemplated to provide sustained-release therapy covering a minimally invasively or surgical procedure to the ligaments, a minimally invasively or surgical procedure within the knee joint addressing any other trauma or knee disorder, and/or therapeutic or prophylactic relief from a trauma or knee disorder which may have resulted from a previous surgical intervention. For example, the present invention may provide for treatment of a disorder of the knee joint such as osteoarthritis or rheumatoid arthritis, or a tear of a cruciate, collateral, or patellar ligament, or any combination thereof (e.g., such as a trauma involving a tear of both the ACL and PCL). To this end, the present invention relates to methods wherein multiple pharmaceutical depot implants may be surgically secured to the anterior cruciate ligament, the posterior cruciate ligament, and/or the patellar ligament, and any combination thereof, so as to afford maximum therapeutic or prophylactic effect from the sustained-release of a biological agent or agents from the respective depot implants.

The biological agent(s) used in the methods of the present invention may be any molecule, cell, or physical stimulus which provides therapeutic or prophylactic relief for acute or chronic pain and/or inflammation associated with knee disorders including, but not limited to, osteoarthritis, rheumatoid arthritis, as well as known traumas associated with the tendons, ligaments and muscles in and around the knee joint. Such agents may include, but are not limited to, a small molecule, an oligonucleotide, an antibody or relevant antibody fragment as disclosed and further discussed herein, siRNA, as well as any factor in the form of a molecule, cell or physical stimulus which regulates expression of a gene of interest or effects stability or activity of the expressed transcript and/or translated protein, so as to modulate the target so as to provide a level of post-operative relief to the knee joint. To this end, these biological agent(s) may be any molecule, cell, or physical stimulus which provides therapeutic or prophylactic relief for acute or chronic pain and/or inflammation associated with any knee trauma or knee disorder, including traumas associated with the tendons, ligaments and muscles in and around the knee joint. In one embodiment, the injury or disorder is associated with an intraarticular ligament (e.g., the ACL and PCL). In another embodiment the trauma or disorder effects other ligaments of the knee joint (including but not limited to the lateral or medial collateral ligaments, as well as the patellar ligament). In other embodiments, the injuries or disorders relate to problems associated with the articular cartilage, such as osteoarthritis, chondromalacia, and rheumatoid arthritis. Another embodiment relates to treating meniscal injuries, such as meniscal tears. Additional embodiments include, but are not limited to, chondral fractures, traumas or injuries associated with the patella, just to name a few. Thus, the methods of the present invention may be utilized to deliver a biological agent to the knee joint area in a prolonged, sustained time frame to provide therapeutic or prophylactic treatment of any trauma or disorder of the knee while strategic placement of the depot implant(s) will provide for normal post-operative articulation of the knee joint.

The biological agent(s) for use in practicing the present invention also includes, but is not limited to, an anti-inflammatory agent, antibiotic and/or analgesic, or combinations thereof, each of which may be presented in a sustained-release formulation as a biological depot. As noted above, any such biological agent may be a molecule, cell or physical stimulus which promotes the intended biological response including, but not limited to, anti-inflammatory agents which are delivered by the methods of the present invention to promote a prolonged, sustained delivery of the agent(s) within the knee joint area. Such anti-inflammatory agents may be in any form such that administration of the entity promotes the desired anti-inflammatory response, including any molecule, cell or physical stimulus which positively effects the activity of an anti-inflammatory response. As discussed herein, a targeted inflammatory cytokine or protein related to the inflammatory response includes, but is not limited to, TNF-α, IL-1β, IL-6, IL-8, NF-κB, High Mobility Group Box 1 (HMG-B1), IL-2, IL-15, and matrix metalloproteinases (MMPs) while a specific anti-inflammatory cytokine or related protein which may promote an anti-inflammatory response includes but is not limited to IL-10, IL-4, IL-13 and TGF-β, as well as any other cytokine or pathway related protein which modulates the respective anti-inflammatory cytokine so as to impart an increase in the ability to reduce inflammation and pain within a joint such as the knee joint.

In one embodiment of the present invention, the anti-inflammatory agent used in the methods of the present invention is an antagonist of TNF-α. Such an agent may be administered surgically as a biological depot implant by any surgical or other attachment procedure known in the art, with a particular embodiment of the methods of the present invention relating to the continuous administration of a TNF-α antagonist via a sustained-release formulation via surgical attachment to a ligament, tendon or muscle within or adjacent to the knee joint. Tumor necrosis factor (herein, TNF-α, and also known as TNF or cachectin) is the prototype member of a large family of proteins with diverse functions. The TNF locus is located within the MHC gene cluster in humans (chromosome 6). More specifically, the gene encoding TNF-α is located within the MHC class IV cluster along with other family members, lymphotoxin-α (LT-α, formally TNF-β) and lymphotoxin-β (for a review, see Ruuls and Sedgwick, 1999, *American J. Human Genetics* 65:294-301). Tumor necrosis factor-alpha is a soluble homotrimer of 17 kD protein subunits, with a 26 kD membrane bound precursor. Tumor necrosis factor-alpha causes a pro-inflammatory cascade, resulting in tissue injury. For example, TNF-α induces an NF-κB-mediated survival and inflammatory pathway. Thus, it is now well known that TNF-α is an inflammatory cytokine; a cytokine secreted from macrophages and monocytes and which is involved in inflammatory diseases (causing a pro-inflammatory response leading to the breakdown of cartilage and bone), autoimmune diseases, bacterial infections, cancers and other degenerative diseases. This cytokine also functions as a signal transmitter in several pathological processes, such as necrosis and apoptosis, is involved in the process of promoting induction of an adhesion molecules, and an increase in the adherence of neutrophils and lymphocytes. To this end, TNF-α has been regarded as a useful target protein for a specific physiological treatment of rheumatoid arthritis, psoriatic arthritis, and ankylosing spondylitis. Therefore, the present invention relates to use of an anti-cytokine agent which is an antagonist of TNF-α. Such a biological agent may be administered in devices known in the art, with a particular embodiment relating to the sustained-release of a TNF-α antagonist via depot implants or depot injection within the knee joint as described herein. Thus, one aspect of the present invention relates to methods of treating traumas or disorders of the knee by sustained, local delivery of an anti-cytokine agent that is a direct and local-acting antagonistic modulator of the pro-inflammatory effect of TNF-a such as, but not limited to, an anti-cytokine agent which is a soluble TNF-a, any pegylated soluble TNF-a, monoclonal or polyclonal antibody or antibody fragment or combination thereof. Suitable examples include, but are not limited to, adalimumab, infliximab, etanercept, pegsunercept (PEG sTNF-R1), sTNF-R1, CDP-870, CDP-571, CNI-1493, RDP58, ISIS 104838, 1?3-β-D-glucans, Lenercept, PEG-sT-NFRII Fc mutein, D2E7, afelimomab, and combinations thereof. A suitable TNF-a antagonist can also prevent or inhibit TNF-a synthesis and/or TNF-a release and includes compounds such as thalidomide, tenidap, and phosphodiesterase inhibitors, such as, but not limited to, pentoxifylline and rolipram. A biological agent may also include any molecule, cell or physical stimulus which positively modulates the activity of the agent known to effect the inflammatory response. These agents can decrease pain through their actions as inhibitors or agonists of the release of pro-inflammatory molecules. For example, these substances can act by inhibiting or antagonizing expression or binding of cytokines or other molecules that act in the early inflammatory cascade, often resulting in the downstream release of prostaglandins and leukotrienes.

In another aspect of the present invention, the anti-cytokine agent is a TNF-a binding protein. One suitable such anti-cytokine agent is currently referred to as onercept. Any formulation comprising onercept, onercept-like agents, and derivatives are all considered acceptable to practice the methods of the present invention. Still other suitable biological agent includes dominant-negative TNF variants. A suitable dominant-negative TNF variant includes, but is not limited, to DN-TNF and including those described by Steed, et al. (2003, *Science*, 301:1895-1898). Still more embodiments include the use of a recombinant adeno-associated viral (rAAV) vector technology platform to deliver the oligonucleotides encoding inhibitors, enhancers, potentiators, neutralizers, or other modifiers. For example, in one embodiment a rAAV vector technology platform delivers the DNA sequence of a potent inhibitor of TNF-a. One suitable inhibitor is TNFR:Fc. Other anti-cytokine agents include antibodies including, but not limited to, naturally occurring or synthetic, double chain, single chained, or fragments thereof, as discussed herein.

It is understood that TNF-a is both affected by upstream events which modulate its production and, in turn, affects downstream events. Alternative approaches to using such a compound is to exploit this fact, and antagonists are designed to specifically target TNF-a as well as molecules upstream, downstream and/or a combination thereof. Such approaches include, but are not limited to, modulating TNF-a directly, modulating kinases, inhibiting cell-signaling, manipulating second messenger systems, modulating kinase activation signals, modulating a cluster designator on an inflammatory cell, modulating other receptors on inflammatory cells, blocking transcription or translation of TNF-a or other targets in pathway, modulating TNF-a post-translational effects, employing gene silencing, or modulating interleukins. Anti-cytokine agents which inhibit TNF-a-post translational effects are useful in the invention. For example, the initiation of a TNF-a signaling cascade results in the enhanced production of numerous factors that subsequently act in a paracrine and autocrine fashion to elicit further production of TNF-a as well as other pro-inflammatory agents (IL-1β, IL-6, IL-8, HMG-B1). Extracellular TNF-a modifying anti-cytokine agents that act on the signals downstream of TNF-a are useful in treating systemic inflammatory diseases. Some of these anti-cytokine agents are designed to block other effector molecules while others block the cellular interaction needed to further induce their production, for example, integrins and cell adhesion molecules. Thus, the present invention also relates to an anti-cytokine which antagonizes, for example, IL-1β, IL-6, IL-8 and HMG-B1.

In another embodiment of the present invention, the anti-inflammatory agent used in the methods of the present invention is an antagonist of interleukin 1-beta (IL-1β). Again, a particular embodiment of the methods of the present invention relates to the prolonged administration of an IL-1β antagonist via a sustained-release pharmaceutical depot implant within the knee joint including, but not limited to, the anterior cruciate ligament, the posterior cruciate ligament, the medial collateral ligament, the lateral collateral ligament, or the patellar ligament. To this end, a portion of the present invention relates to an anti-cytokine agent which antagonizes the IL-1β-induced pro-inflammatory response. Interleukin 1-beta is a cytokine which shows a similar biological response compared to TNF-a. For example, certain inhibitors of this protein are similar to those developed to inhibit TNF-a. One such example is Kineret® (anakinra) which is a recombinant, non-glycosylated form of the human interleukin-1 receptor antagonist (IL-1Ra). Another way to incorporate use of IL-1Ra is to deliver an autologous blood serum, such as Orthokine®. Orthokine® serum is derived from the human patient's blood, which naturally contains IL-1Ra. The blood is removed, cultured in vitro to promote stimulation of monocytes and in turn increase production of IL-1Ra. The protein is extracted and then delivered back to the patient. In addition to use of IL-1Ra to antagonize IL-1, other suitable anti-cytokine agents may take the form as those described above regarding TNF-α. For example, a suitable anti-cytokine agent targeting IL-1 is an antibody against IL-1 which is effective in antagonizing the ability of IL-1 to interact with the type I or type II IL-1 receptor. Such an antibody includes, but is not limited to, AMG 108, a monoclonal antibody that blocks IL-1 activity. Any such antibody or antibody fragment, as discussed herein, will be useful to practice the methods of the present invention.

In another embodiment of the present invention, the anti-inflammatory agent used in the disclosed methods is an antagonist of interleukin-6 (IL-6). An antagonist of IL-6 for use in this portion of the invention may be any form of a biological agent as described herein. Interleukin-6 (IL-6) is a multifunctional cytokine that plays a central role in host defense due to its wide range of immune and hematopoietic activities and its potent ability to induce the acute phase response. Overexpression of IL-6 has been implicated in the pathology of a number of diseases including multiple myeloma, rheumatoid arthritis, Castleman's disease, psoriasis, and post-menopausal osteoporosis. To this end, selective antagonists of IL-6 activity will be useful as an anti-inflammatory in the methods of the present invention. A selective antagonist may be any such anti-cytokine agent as disclosed herein including, but not limited to, an antibody against IL-6 such as a humanized anti-IL-6 mAb (MRA, tocilizumab, Chugai); or a human monoclonal antibody against IL-6, or an IL-6 'trap', which would contain two soluble IL-6 receptors fused to an IgG molecule (i.e., Fc fragment) to produce an IL-6 dimer. Notwithstanding the foregoing, and as noted with other embodiments, the anti-cytokine agent which antagonizes IL-6 may come in any form disclosed herein, as well as any molecule, cell or physical stimulus which promotes the ability of such an agent to antagonize IL-6.

A further embodiment of the present invention contemplates administering an effective amount of an antagonist of interleukin-8 (IL-8) to the patient. Thus, the methods of promoting a sustained-release of a biological agent(s) within the knee joint will include administering to the subject an effective amount of an antagonist of a CXC chemokine involved in neutrophil infiltration. Interleukin-8, a 72 amino acid, tissue-derived peptide secreted by several types of cells in response to inflammatory stimuli, is a chemokine wherein 2 cysteines are separated by a single amino acid, thus referred to as a CXC chemokine. Chemokines of the CXC family show specificity for neutrophils, and to an extent, lymphocytes. Interleukin-8 is known to be directly involved in late cytokine activation of polymorphonuclear neutrophils (PMNs), leading to neutrophil activation and migration later in the inflammation cascade. To this end, an embodiment of the present invention relates to use of an anti-cytokine agent which acts as an antagonist of interleukin-8 (IL-8) to be administered to a patient to treat inflammation associated with a trauma or disorder of the knee. As noted with other embodiments, the anti-cytokine agent which antagonizes IL-8 may come in any form disclosed herein, as well as any molecule, cell or physical stimulus which promotes the ability of such an agent to antagonize IL-8.

Another embodiment of the methods of the present invention relate to utilizing a biological agent which is an antagonist of Nuclear Factor kappa B (NF-?B). Nuclear Factor kappa B is a transcription factor involved in cellular responses to stimuli such as stress, cytokines, free radicals, ultraviolet irradiation, and bacterial or viral antigens. Nuclear Factor kappa B regulates inflammation, dendritic cell development and function, thymic selection and regulatory T cell production. There are five mammalian NF-?B family members which exist as homodimers or heterodimers: NF-?B1 (p50), NF-?B2 (p52), RelA (p65), RelB and c-Rel. All members share a Rel homology domain in their N-terminal region. RelA, RelB and c-Rel also have contain a trans-activation domain in their C-terminus. The NF-?B1 and NF-?B2 proteins are synthesized as larger precursors (p105 and p100, respectively) which undergo processing to generate the mature NF-?B subunits, p50 and p52. The processing of p105 and p100 is mediated by the ubiquitin/proteasome pathway and involves selective degradation of their C-terminal region containing ankyrin repeats. An active NF-?B transcription factor promotes expression of a number of genes, many of which participate through the canonical pathway to mediate the immune response, including cytokines such as TNF-α, IL-1β, IL-6 and GM-CSF and chemokines such as IL-8, RANTES, ICAN-1 and E-selectin. Again, the anti-cytokine agent which antagonizes NF-?B may come in any form disclosed herein, as well as any molecule, cell or physical stimulus which promotes the ability of such an agent to antagonize NF-?B such as, but not limited to, sulindac, clonidine, or dexamethasone. Additional anti-cytokine agents include, but are in no way limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, HMGB-1 mAb (Critical Therapeutics Inc.), anti-IL2R antibody (daclizumab, basiliximab), ABX (anti IL-8 antibody), HuMax IL-15 (anti-IL 15 antibody), NF-?B inhibitors such as for example glucocorticoids such as flucinolonone, antioxidants, such as dithiocarbamate, and other compounds such as sulfasalazine [2-hydroxy-5-[-4-[C2-pyridinylamino)sulfonyl]azo]benzoic acid], and clonidine.

A further embodiment of the present invention contemplates administering an effective amount of an inhibitor of a matrix metalloprotease (MMP) to the patient. Most MMP inhibitors are thiols or hydroxamates. Non-limiting examples of MMP inhibitors include TAPI-1 (TNF-a protease inhibitor) which blocks cleavage of cell surface TNF; TAPI-0, an analog of TAPI-1 that possesses similar efficacy in vitro; TAPI-2 which is inhibits both the activation-induced shedding of L-selectin from neutrophils, eosinophils, and lymphocytes and also inhibits phenylarsine oxide-induced L-selectin shedding; Ac-SIMP-1; Ac-SIMP-2; SIMP-1; SIMP-2; doxycycline; marimastat (British Biotech); cipemastat (Roche); and tissue inhibitor of metalloproteinases (TIMPs) which include TIMP-1, TIMP-2, TIMP-3 and TIMP-4. Synthetic inhibitors of MMPs generally contain a chelating group which binds the catalytic zinc atom at the MMP active site tightly. Common chelating groups include hydroxamates, carboxylates, thiols, and phosphinyls.

Another biological agent which may be considered when practicing the methods of the present invention relate to administering a pharmaceutically effective amount of interleukin-10 (IL-10). Interleukin-10 is an anti-inflammatory cytokine which will promote reduction of inflammation and pain. This non-limiting embodiment relates to administration of IL-10, or any biologically active fragment thereof as well as any molecule, cell or physical stimulus which promotes the ability IL-10 to impart the intended anti-inflammatory effect to the target patient by methods and drug delivery devices as described herein. Interleukin-10 is a homodimer with a molecular mass of 37 kDa. Each monomer consists of an identical 160 amino acid protein with a molecular mass of 18.5 kDa. Interleukin-10 is known as an important immunoregulatory cytokine which is expressed in numerous cell populations, with its main function seeming to be related to limitation and termination of inflammatory responses, as well as regulating the differentiation and proliferation of various immune cell types (for a review, see Asadullah, et al., 2003, *Pharmacological Reviews* 55(2):241-269). As noted by Asadullah, et al. (id.), it has been shown in several ex vivo studies that IL-10 can effectively block TNF-α, IL-1 and IL-8 by synovial macrophages and synoviocytes.

In an alternative embodiment, the biological agent of the present invention may be a growth factor. The growth factor may be an osteoinductive and/or cartilage forming protein or molecule that may be used alone or in combination with any of the above agents to stimulate or induce bone or cartilage growth within the joint. Platelet-derived growth factors (PDGFs), bone morphogenetic proteins (BMPs), growth differentiation factor proteins (GDFs) insulin-like growth factors (IGFs), basic fibroblast growth factor (bFGF), cartilage derived morphogenetic protein (CDMP), and various other bone and cartilage regulatory proteins, such as CD-RAP or the like, are all growth factors that are successful in bone and cartilage regeneration. BMPs and CDMPs, in particular, induce new cartilage and bone formation though a signal cascade that, ultimately, leads to morphogenesis of precursor cells into bone or cartilage cells. CD-RAP is also known to be a regulatory protein synthesized by chondrocytes involved in the formation of type II collagen and, ultimately, cartilage. To this end, BMPs, GDFs, CDMPs, and CD-RAP may be contained within the depot of the present invention and released from the depot in accordance with the methods of the present invention such that the proteins or molecules induce the formation of bone and/or cartilage. Such formation of bone and/or cartilage leads to the treatment of the degeneration of cartilage and bone associated with osteoarthritis, chondromalacia, rheumatoid arthritis, or any other bone or cartilage degenerative condition.

Examples of such BMPs and CDMPs as discussed herein may include, but are not limited to, BMP-2, BMP-4, BMP-6, BMP-7, BMP-8, and CDMP-1. The BMPs or CDMPs may be available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. the contents of which are incorporated herein by reference. All osteoinductive factors are contemplated whether obtained as above or isolated from bone. Methods for isolating BMP from bone are described in U.S. Pat. No. 4,294,753 to Urist and Urist et al., 81 PNAS 371, 1984 the contents of which are incorporated herein by reference.

The present invention is not limited to the above embodiments of BMPs, CDMPs, and CD-RAP. Rather, any natural or synthetic BMP, CDMP or other osteoinductive or cartilage producing protein or molecule is contemplated by the present invention such as, but not limited to, BMP-1, BMP-2, rhBMP-2, BMP-3, BMP-4, rhBMP-4, BMP-5, BMP-6, rhBMP-6, BMP-7 [OP-1], rhBMP-7, BMP-8, BMP-9, BMP-10, BMP-11, BMP-12, BMP-13, BMP-14, BMP-15, BMP-16, BMP-17, BMP-18, growth differentiation factor 5 (GDF-5) [CDMP-1], rhGDF-5, GDF-6, and GDF-7. Additionally, the present invention may include, separately or in combination with any of the above embodiments, any other protein or molecule that induces bone or cartilage regeneration such as, but not limited to, platelet-derived growth factors (PDGFs), bone morphogenetic proteins (BMPs), insulin-like growth factors (IGFs), fibroblast growth factor (FGF), cartilage derived morphogenetic protein (CDMP), LIM mineralization proteins, transforming growth factors (TGF), fibroblast growth factor (FGF), and growth differentiation factors (GDF). A more detailed discussion as to how each of these growth factors and/or proteins induce bone and cartilage regeneration may be found in Rengachary, 2002, *Neurosurg. Focus,* 13:1-6; Reddi, 2001, *Arthritis Res,* 3:1-5; Varkey et al., 2004, *Expert Opin. Drug Deliv.,* 1:19-36, the contents of which are incorporated herein by reference.

In additional embodiments of the invention, a biological agent may also include, but not be limited to, an antibiotic or an analgesic, or any combination thereof. Non limited examples of antibiotics include, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, timidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof. Non-limiting suitable analgesics include morphine and naloxone, local anaesthetics (such as, for example, lidocaine, glutamate receptor antagonists, adrenoreceptor agonists, adenosine, canabinoids, cholinergic and GABA receptors agonists, and different neuropeptides. The above listed antibiotics and analgesics are not intended to be limiting. As such, an antibiotic or analgesic of the present invention may include any antibiotic or analgesic listed in any current or previous Physicians' Desk Reference. Moreover, a detailed discussion of different analgesics is provided in Sawynok et al., 2003, *Pharmacological Reviews*, 55:1-20, the content of which is incorporated herein by reference.

Additionally, suitable anti-inflammatory compounds for use in the present invention may include the compounds of both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, and triamcinolone. Mixtures of the above steroidal anti-inflammatory compounds can also be used.

Moreover, non-limiting examples of non-steroidal anti-inflammatory compounds that may be used in the present invention include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone. The various compounds encompassed by this group are well-known to those skilled in the art. For detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference. Finally, mixtures of these non-steroidal anti-inflammatory compounds may also be employed, as well as the pharmacologically acceptable salts and esters of these compounds.

In yet other embodiments, further excipients are employed. The amount of excipient that is useful in the composition of this invention is an amount that serves to uniformly distribute the anti-cytokine agent, anti-inflammatory cytokine or related agent, and any other active ingredient, throughout the composition so that it can be uniformly dispersed when it is to be delivered to a subject in need thereof. It may serve to dilute an active ingredient to a concentration at which the appropriate active ingredient(s) can provide the desired beneficial palliative or curative results while at the same time minimizing any adverse side effects that might occur from too high a concentration. It may also have a preservative effect. Thus, for the active ingredient(s) having a high physiological activity, more of the excipient will be employed. On the other hand, for any active ingredient(s) that exhibit a lower physiological activity, a lesser quantity of the excipient will be employed. In general, the amount of excipient in the composition will be between about 50% weight (w) and 99.9% w. of the total composition. Of course, if the anti-cytokine agent, anti-inflammatory cytokine or related agent, and any other active ingredient exhibits a particularly low physiological activity, the amount of excipient could be as little as 1% w. On the other hand, for such an active ingredient(s) that has a particularly high physiological activity, the amount of excipient may be between about 98.0% and about 99.9% w. In addition, the biological agent(s) may by administered in the form of a "chemical derivative" (a molecule that contains additional chemical moieties which are not normally a part of the base molecule). Such moieties may improve the solubility, half-life, absorption, etc. of the biological agent. Alternatively, these moieties may attenuate undesirable side effects of the biological agent. The methods for preparation of a formulation described herein including, but not limited to, a sustained-release formulation, will be known in the art, and are disclosed in references cited herein, as well as *Remington's Pharmaceutical Sciences* (18th ed.; Mack Publishing Company, Easton, Pa., 1990), the contents of which are incorporated herein by reference.

Drug delivery systems may be provided to a subject by a variety of routes. These systems are usually split into five general groups: inhaled, oral, transdermal, parenteral and suppository. Inhaled devices include gaseous, misting, emulsifying and nebulizing bronchial (including nasal) inhalers; oral devices include mostly pills; whereas transdermal devices include mostly patches. The methods of the present invention rely on parenteral administration routes and more specifically on implant depots or depot injections which provide for prolonged release of the biological agent within the knee joint, such as in or around a damaged ligament or within the synovial space. Devices for use in these parenteral delivery systems include non-injectable and injectable devices. Non-injectable devices may be described herein as an "implant", "pharmaceutical depot implant", "depot implant", "non-injectable depot" or some such similar term. Common depot implants may include, but are not limited to, solid biodegradable and non-biodegradable polymer devices (such as an extended polymer or coaxial rod shaped device and/or a microsphere), as well as numerous pumps and micropump systems also known in the art. Injectable devices are split into bolus injections (release and dissipation of the drug subsequent to injection), and repository or depot injections, which provide a storage reservoir at the site of injection, allowing for sustained-release of the biological agent over time.

In one embodiment, a sustained-release drug delivery device for use in practicing the methods of the present invention is a depot implant. Such an implant may be inserted within the knee joint, preferably being surgically secured to a cruciate, collateral or patellar ligament by a suture, suture-anchor combination or any other means understood in the art to secure a depot to soft tissue. The implantation of such a device will be in such a manner as to allow for normal joint articulation in the post-operative setting while also acting as an adequate reservoir for the prolonged release of the biological agent(s) during the prescribed rehabilitation period. This drug delivery device will be capable of carrying the drug formulation in such quantities as therapeutically or prophylactically required for treatment over the pre-selected period. The depot implant may also provide protection to the formulation from degradation by body processes (such as proteases) for the duration of treatment. As known in the art, the term "sustained-release" refers to the gradual (continuous or discontinuous) release of such an agent from the block polymer matrix over an extended period of time. The sustained-release of the contemplated biological agent(s), carrier and/or excipient will result in a local, biologically effective concentrations of the agent(s) in or around the damaged ligament or tendon, or in the vicinity of the patellar, cruciate and/or collateral ligaments, which may act as points of attachment for the depot implant. A sustained release of the biological agent(s) will be for a period of a single day, several days, a week or more, a month or more, or up to about twelve or eighteen months, depending on the formulation.

The surgical or non-surgical attachment of a non-injectable implant to a cruciate, collateral or patellar ligament represents a core strategy for practicing the methodology disclosed within this specification. As noted above, this type of depot implant may take the form of a solid biodegradable or degradable polymer device, or may be in the form of a pump or a micropump device or devices which can be secured to the appropriate ligament(s) so as to promote prolonged availability of the biological agent within the knee joint area while not affecting normal knee joint articulation during the rehabilitation process. Natural or synthetic polymers known in the art will be useful due to characteristics such as versatile degradation kinetics, safety, and biocompatibility. These copolymers can be manipulated to modify the pharmacokinetics of the active ingredient, shield the agent from enzymatic attack, as well as degrade over time at the site of attachment or injection. The artisan will understand that there are ample teachings in the art to manipulate the properties of these copolymers, including the respective production process, catalysts used, and final molecular weight of the sustained-release depot implant or depot injection. Natural polymers include, but are not limited to, proteins (e.g., collagen, albumin or gelatin); polysaccharides (cellulose, starch, alginates, chitin, chitosan, cyclodextrin, dextran, hyaluronic acid) and lipids. Biodegradable synthetic polymers may include, but are not limited to, various polyesters, copolymers of L-glutamic acid and gamma ethyl-L-glutamate (Sidman et al., 1983, *Biopolymers* 22:547-556), polylactides ([PLA]; U.S. Pat. No. 3,773,919 and EP 058,481), polylactate polyglycolate (PLGA) such as polylactide-co-glycolide (see, for example, U.S. Pat. Nos. 4,767,628 and 5,654,008), polyglycolide (PG), polyethylene glycol (PEG) conjugates of poly (α-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described above (see, for example, U.S. Pat. No. 6,991,654 and U.S. Pat. Appl. No. 20050187631, each of which is incorporated herein by reference in its entirety), hydrogels (see, for example, Langer et al., 1981, *J. Biomed. Mater. Res.* 15:167-277; Langer, 1982, *Chem. Tech.* 12:98-105, non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(−)-3-hydroxybutyric acid (EP 133,988), hyaluronic acid gels (see, for example, U.S. Pat. No. 4,636,524), alginic acid suspensions, polyorthoesters (POE), and the like. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Amidox (PLA; periodontal disease), Nutropin Depot (PLGA; with hGH), and the Trelstar Depot (PLGA; prostate cancer). Other synthetic polymers included, but are not limited to, poly(c-caprolactone), poly-3-hydroxybutyrate, poly(β-malic acid) and poly(dioxanone); polyanhydrides, polyurethane (see WO 2005/013936), polyamides, cyclodestrans, polyorthoesters, n-vinyl alcohol, polyethylene oxide/polyethylene terephthalate, polyphosphazene, polyphosphate, polyphosphonate, polyorthoester, polycyanoacrylate, polyethylenegylcol, polydihydropyran, and polyacytal. Non-biodegradable devices include, but are not limited to, various cellulose derivatives (carboxymethyl cellulose, cellulose acetate, cellulose acetate propionate, ethyl cellulose, hydroxypropyl methyl cellulose), silicon-based implants (polydimethylsiloxane), and acrylic polymers (polymethacrylate, polymethylmethacrylate, polyhydroxy (ethylmethylacrylate)), as well as polyethylene-co-(vinyl acetate), poloxamer, polyvinylpyrrolidone, poloxamine, polypropylene, polyamide, polyacetal, polyester, poly(ethylene-chlorotrifluoroethylene), polytetrafluoroethylene (PTFE or Teflon™), styrene butadiene rubber, polyethylene, polypropylene, polyphenylene oxide-polystyrene, poly-a-chloro-p-xylene, polymethylpentene, polysulfone and other related biostable polymers.

Thus, the polymers utilized to practice the methods of the present invention may include natural, biodegradable, or biostable polymers, or combinations thereof. Such polymers may be liquid or solid and may be formed into monolithic or coaxially extruded rods, as illustrated in FIGS. 1-5, impregnated with drug. The extruded rod is implanted in the subject using either standard surgical techniques such as by suture or a suture-anchor combination device deployed through the ligament(s) or non-surgical, minimally invasive techniques. Non-injectable implants include preformed monolithic or coaxially extruded rods or microspheres made of biodegradable polymer impregnated with drug. These rods or spheres may be prepared by melt extrusion or other techniques well known to those skilled in the art. A single embodiment may include a depot implant which is a monolithic rod or sphere may be prepared by melt extrusion of a specific agent-polymer mix, whereby the extruded rod is implanted within the knee joint using either standard surgical or minimally invasive techniques under general or local anesthetic to secure the implant to a cruciate, collateral or patellar ligament. Another embodiment regarding a depot implant would be the use of a coaxial rod, in which there is drug in the core as well as the sheath. Again, the polymer could be any suitable polymer, as noted above, which may be determined by one of skill in the art. The depot is not limited to a rod or microsphere but may be a disc, a cylinder, or any other shape understood in the art to act as a sustained-release drug device or depot. In another embodiment, the methods of the present invention may be presented in a sustained-release formulation as a repository or depot injection. Carriers suitable for sustained-release depot formulations include, but are not limited to, microspheres, films, capsules, particles, gels, coatings, matrices, wafers, pills or other pharmaceutical delivery compositions. Examples of such sustained-release formulations are described above. See also U.S. Pat. Nos. 6,953,593; 6,946,146; 6,656,508; 6,541,033; and 6,451,346, the contents of each which are incorporated herein by reference. The dosage form must be capable of carrying the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of normal joint articulation and other movements by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g., where the dosage form is implanted, it is substantially non-reactive with respect to a subject's body or body fluids). Generally, the respective biological agent(s) is administered to an individual for at least 12 hours to at least a week, and most likely via an implant designed to deliver a drug for at least 10, 20, 30, 100 days or at least 4 months, or at least 6 months, or at least twelve to eighteen months or more, as required. In various embodiments of the invention and various aspects thereof, the biological agent, depending on the drug of the drug formulation administered, is delivered at a low dose, e.g., from about 0.01 µg/hr or 0.1 µg/hr, 0.25 µg/hr, 1 µg/hr, generally up to about 200 µg/hr, or the drug formulation is delivered at a low volume rate e.g., a volume rate of from about 0.001 ml/day to about 1 ml/day. Specific ranges of amount of drug delivered will vary depending upon, for example, the potency and other properties of the drug (i.e., protein therapeutic, IgG antibody therapeutic, small molecule, etc.) used and the therapeutic requirements of the subject.

Figure 2:
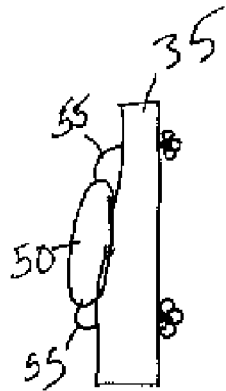
FIG. 2 illustrates a side view of a first embodiment of a depot tethered to an ACL with a suture.
Figure 8:
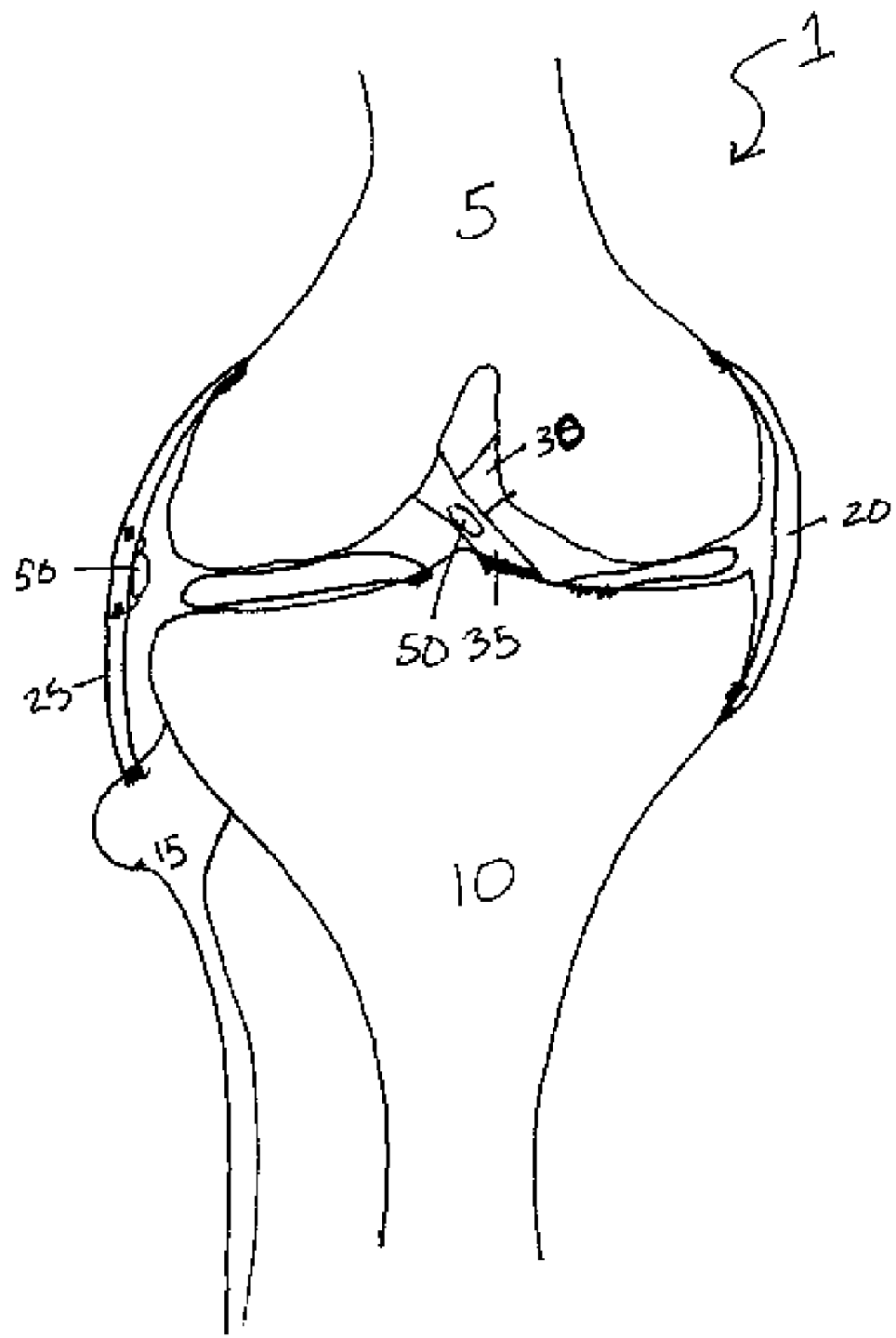
FIG. 8 illustrates a front view of a right knee joint with one depot tethered to the ACL and another tethered to the lateral collateral ligament.

Referring to FIG. 2, in a first embodiment the depot may be comprised of a monolithic or coaxially extruded rod 50. At least one suture 55 may extend from either or both of the ends of the rod 50. The sutures 55 may be comprised of any natural or synthetic, biocompatible and biodegradable polymer, or of any material understood in the art to secure a depot to soft tissue. The suture 55 may also extend from the center of the depot or any location on the depot understood to secure the depot to the soft tissue. In operation, FIGS. 2 and 8 illustrate the product of one method of securing the depot to the ACL 35 by tying the depot to the ACL 35 such that the depot is positioned in the center of the ACL 35 to ensure uniform distribution of the biological agent within the synovial joint. The suture 55 may secure the depot to the ACL 35 by threading the suture(s) through microincisions in the ligament, by tying the suture(s) substantially around the ligament, or any similar method understood in the art to suture a depot to soft tissue without interfering with the normal articulation of the joint. The rod 50 may be secured to the ACL 35 distal to the PCL 30 such that the depot does not interfere with the PCL 30. The method of tying the depot 50 to the ligament is not limited to the illustrations in FIGS. 2 and 8 and may be any method understood in the art to suture a depot to soft tissue.

Figure 3:
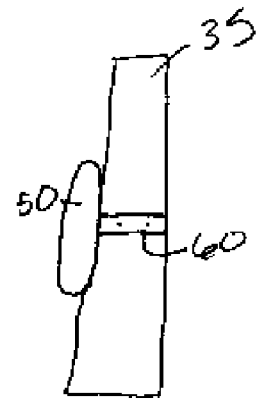
FIG. 3 illustrates a side view of a second embodiment of a depot tethered to an ACL with a strap or clasp.

Referring to FIG. 3, in a second embodiment the depot may be comprised of a rod 50 with at least one strap or clasp 60 extending from the rod 50. The strap/clasp 60 may be comprised of any natural or synthetic, biocompatible and biodegradable polymer, or of any material understood in the art to secure a depot to soft tissue using a strap/clasp 60. The strap/clasp 60 may extend from the center of the rod 50 or from any location on the rod 50 understood to secure the rod 50 to the soft tissue. In operation, the strap/clasp 60 may be secured to a ligament, such as the ACL 35, within the joint capsule. FIGS. 3 and 8 illustrate the product of one method of securing the depot to the ACL 35 such that the strap/clasp 60 substantially surrounds the ACL 35. Moreover, the depot is positioned in the center of the ACL 35 to ensure uniform distribution of the biological agent within the synovial joint. The rod 50 may also be secured to the ACL 35 distal to the PCL 30, or in any location, such that the depot does not interfere with the PCL 35. However, the product of the method of securing the depot 50 to the ligament is not limited to the illustration in FIGS. 3 and 8 and may be any method understood in the art to suture a depot to soft tissue using a strap or clasp.

Figure 4:
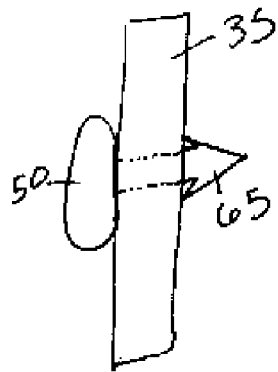
FIG. 4 illustrates a side view of a third embodiment of a depot tethered to an ACL with a barb.

Referring to FIG. 4, in a third embodiment the depot may be comprised of a rod 50 with at least one barb 65 extending from the rod 50. The barb 65 may be comprised of any natural or synthetic, biocompatible and biodegradable polymer, or of any material understood in the art to secure a depot to soft tissue using at least one barb 65. The barb 65 may extend from the center of the rod 50 or from any location on the rod 50 understood to secure the rod 50 to the soft tissue. In operation, the barb 65 is secured to a ligament, such as the ACL 35, within the joint capsule. FIG. 4 illustrates one method of securing the depot to the ACL 35 wherein the barb 65 is threaded through a microincision in the ACL 35. The depot is positioned in the center of the ACL 35 to ensure uniform distribution of the biological agent within the synovial joint. The rod 50 may also be secured to the ACL 35 distal to the PCL 30 or at any location of the ACL 35 so long as the depot does not interfere with the PCL 30. However, the method of securing the depot 50 to the ligament is not limited to the illustration in FIG. 4 and may be any method understood in the art to secure a depot to soft tissue using a barb.

Figure 5:
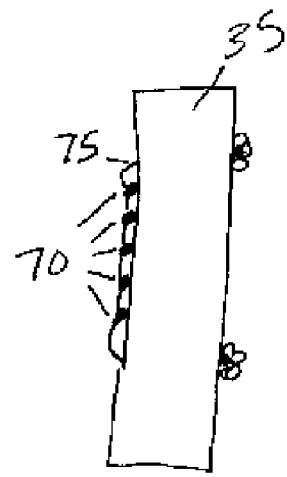
FIG. 5 illustrates a side view of a fourth embodiment of a depot tethered to an ACL with a suture wherein the depot is a series of microspheres.

Referring to FIG. 5, in a fourth embodiment the depot may be comprised of at least one microparticle, such as a microsphere 70. At least one suture 75 extends from either or both of the ends of the microsphere(s) 70 wherein the suture couples together multiple microspheres, if there are more than one, and/or couples the microsphere(s) 70 to the ligament. The suture(s) 75 may be comprised of any natural or synthetic, biocompatible and biodegradable polymer, or of any material understood in the art to secure a depot to soft tissue using at least one suture(s) 75. In operation, FIG. 5 illustrates the product of one method of securing the depot to the ACL 35 by tying the depot to the ACL 35 such that the depot is positioned in the center of the ACL 35 to ensure uniform distribution of the biological agent within the synovial joint. Moreover, the microsphere(s) 70 may be secured to the ACL 35 distal to the PCL 30 or in any location of the ACL 35 so long as the depot does not interfere with the PCL 30. However, the method of tying the depot 50 to the ligament is not limited to the illustration in FIG. 5 and may be any method understood in the art to suture a depot to soft tissue.

Figure 6:
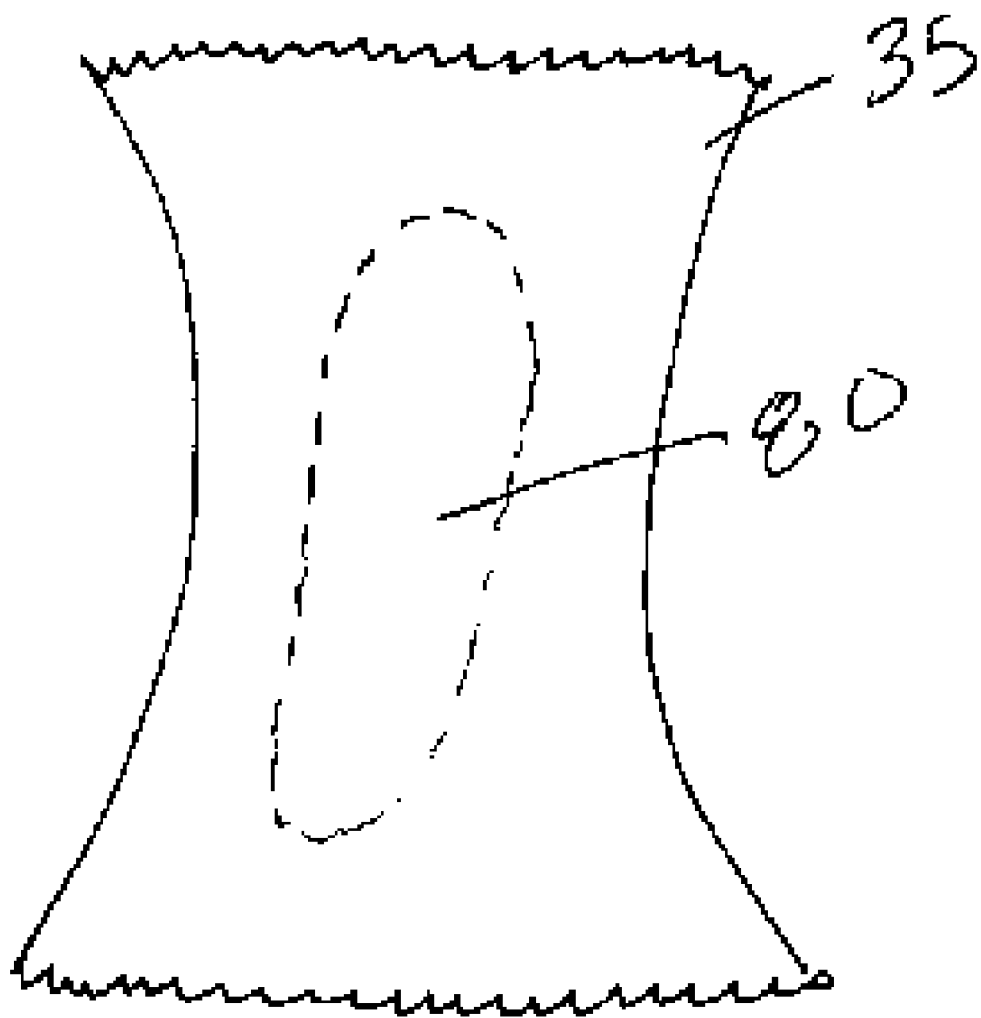
FIG. 6 illustrates a front view of an embodiment of an injectable depot gel wherein the gel is polymerized within an ACL.

Referring to FIG. 6, an embodiment of an injectable depot may be comprised of a flexible gel 80. The flexible gel 80 may be a natural or synthetic polymer as discussed above wherein the gel 80 is injectable into a ligament, such as the ACL 35, such that it sets or polymerizes within the ligament. As illustrated in FIG. 6, the depot may be positioned in the center of the ACL 35 to ensure uniform distribution of the biological agent within the synovial joint. However, the injectable depot is not limited to a gel and may be comprised of any of the injectable structures discussed above or any similar structure known in the art.

Figure 7:
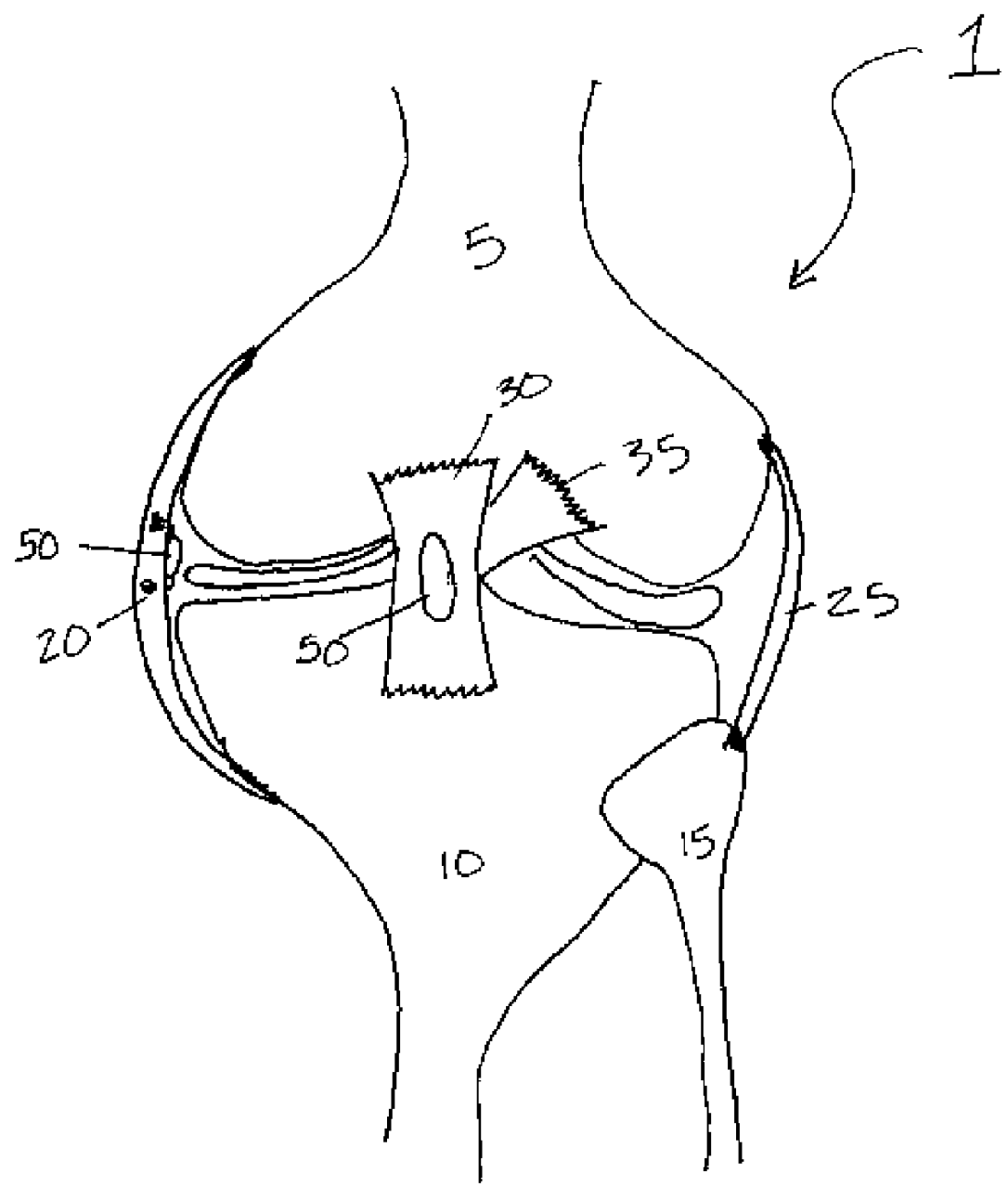
FIG. 7 illustrates a rear view of a right knee joint with one depot tethered to the PCL and another tethered to the medial collateral ligament.

The above embodiments of the depot are not intended to limit the structure of the depot. Rather the depot may be comprised of any other structure understood in the art to embody a sustained release pharmaceutical depot wherein the depot may be tethered or secured to the ligament of the joint of a subject. Moreover, the depot is not limited to being secured to the ACL as discussed above. Rather, as illustrated in FIG. 7, the depot may be secured to the PCL 30 distal to the ACL 35 or at any location of the PCL 30 so long as the depot does not interfere with the ACL 35. In a further embodiment, referring to FIG. 7, the depot may be secured to the medial collateral ligament 20 such that the depot is within the synovial space of the joint and does not interfere with the joint capsule. In another embodiment, referring to FIG. 8, the depot may be secured to the lateral collateral ligament 25 such that the depot is within the synovial space and does not interfere with the joint capsule. In a further embodiment, the depot may be secured to the patellar ligament (not illustrated) such that the depot does not interfere with the normal function of the joint. Finally, in a further embodiment, multiple pharmaceutical depot implants may be secured to the ACL 35, PCL 30, the patellar ligament, the medial collateral ligament 20, and/or the lateral collateral ligament 25 and any combination thereof, so as to afford maximum therapeutic or prophylactic effect from the sustained-release of a biological agent from the respective depot implant(s).

Thus, one object of the present invention is the use of sustained-delivery devices to aid in the treatment of a knee trauma and/or disorder, where parenteral administration of such a device is accomplished while maintaining normal articulation of the knee joint. One advantage to the present invention is that such implantable dosage forms have another benefit in that they reduce the risk of infection associated with external pumps or other methods that require repeated breaking of the skin and/or maintenance of a port for administration. A second advantage is that use of a sustained-release drug delivery device obviates the need for regular dosing by the patient, thus increasing patient compliance with a prescribed therapeutic regimen, and in particular compliance with a prophylactic regimen prescribed prior to the onset of symptoms. Long-term delivery from an implanted dosage form provides an effective and inexpensive method of providing prophylactic care to such populations including, but not limited to, situations whereby a biological agent is delivered to prevent the onset of osteoarthritis. Another advantage of the invention is that the biological agent can be delivered continuously with accuracy and precision and at low quantities as to permit long-term use, especially as an anti-inflammatory, antibiotic and/or analgesic. A further advantage is that a therapeutically effective dose of a biological agent can be delivered at such relatively low volume rates, e.g., from about 0.001 ml/day to 1 ml/day so as to minimize tissue disturbance or trauma near the site where the formulation is released. The formulation may be released at a rate of, depending on the specific biological agent(s), at a low dose, e.g., from about 0.01 µg/hr or 0.1 µg/hr, 0.25 µg/hr, 1 µg/hr, generally up to about 200 µg/hr, or the formulation is delivered at a low volume rate e.g., a volume rate of from about 0.001 ml/day to about 1 ml/day. for example, 0.01 micrograms per day up to about 20 milligrams per day. Dosage depends on a number of factors such as potency, bioavailability, and toxicity of the respective biological agent(s). These and other objects, advantages and features of the present invention will become apparent to those persons skilled in the art upon reading the details of the methodology and compositions as more fully set forth below.

It will be appreciated that suitable carriers, excipients, and other agents may, optionally, be incorporated to formulate the pharmaceutical compositions to provide improved transfer, delivery, tolerance, and the like. The methods of incorporating the biological agent and/or additional active ingredient(s) into the carrier are known to a person of ordinary skill in the art and depend on the nature of the biological agent and the nature of the carrier selected by a person practicing the current invention. Ionic binding, gel encapsulation or physical trapping inside the carrier, iontophoresis and soaking the carrier in a solution of the biological agent are suitable examples contemplated in formulating a pharmaceutical composition to be used to practice of the disclosed treatment methods. Alternatively, the carrier may be little more than a diluent for the biological agent. These formulations may include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular biological agent thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. Any of the foregoing formulations may be appropriate in treatments and therapies in accordance with the present invention, provided that the active ingredient in the formulation is not inactivated by the formulation and the formulation is physiologically compatible.

Administration of an antibody as a biological agent is also contemplated when practicing the methods of the present invention. An antibody may take one of numerous forms known in the art. Antibodies may take the form of any type of relevant antibody fragment, antibody binding portion, specific binding member, a non-protein synthetic mimic, or any other relevant terminology known in the art which refers to an entity which at least substantially retains the binding specificity/neutralization activity. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof including, but not limited to, Fab, F(ab')2, Fv, and scFv (single chain or related entity), which are capable of binding to the respective targeted cytokine. Therefore, it is well known in the art, and is included as review only, that an "antibody" refers to a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise a framework (FW) and complementarily determining regions (CDR). The four FW regions are relatively conversed while CDR regions (CDR1, CDR2 and CDR3) represent hypervariable regions and are arranged from $NH_2$ terminus to the COOH terminus as follows: FW1, CDR1, FW2, CDR2, FW3, CDR3, FW4. The variable regions of the heavy and light chains contain a binding domain that interacts with an antigen while, depending of the isotype, the constant region(s) may mediate the binding of the immunoglobulin to host tissues or factors. That said, also included in the working definition of "antibody" are chimeric antibodies, humanized antibodies, a recombinant antibody, as human antibodies generated from a transgenic non-human animal, as well as antibodies selected from libraries using enrichment technologies available to the artisan. Antibody fragments are obtained using techniques readily known and available to those of ordinary skill in the art, as reviewed below. Therefore, an "antibody" is any such entity or specific binding member, which specifically binds to the respective target cytokine so as to inhibit the ability of the cytokine to impart a normal inflammatory response. Any such entity is a candidate for therapeutic applications disclosed herein. Therefore, the term "antibody" describes an immunoglobulin, whether natural or partly or wholly synthetically produced; any polypeptide or protein having a binding domain which is, or is substantially homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd and diabodies, as discussed without limitation, infra. It is known in the art that it is possible to manipulate monoclonal and other antibodies and use techniques of recombinant DNA technology to produce other antibodies or chimeric molecules which retain the specificity of the original antibody. Such techniques may evolve introducing DNA encoding the immunoglobulin variable region, or the complementarily determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced. Antibodies can be modified in a number of ways, and the term "antibody" should be construed as covering any specific binding member or substance having a binding domain with the required specificity. Thus, this term covers antibody fragments, derivatives, functional equivalents and homologues of "antibody" including any polypeptide comprising an immunoglobulin binding domain, whether natural or wholly or partially synthetic. Such an entity may be a binding fragment encompassed within the term "antigen-binding portion" or "specific binding member" of an antibody including, but not limited to, (i) a Fab fragment, a monovalent fragment consisting of the VL, VH, CL and CH domains; (ii) a F(ab')2 fragment, a bivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody (v) a dAb fragment, which comprises a VH domain; (vi) an isolated complementarily determining region (CDR); (vii) a 'scAb', an antibody fragment containing VH and VL as well as either CL or CH; and (viii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application Publication No. WO 02/32925). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)).

Polyclonal or monoclonal antibodies for use in the disclosed treatment methods may be raised by known techniques. Monospecific murine (mouse) antibodies showing specificity to a conformational epitope of a target of choice may be purified from mammalian antisera containing antibodies reactive against this region, or may be prepared as monoclonal antibodies using the technique of Kohler and Milstein (1975, *Nature* 256: 495-497). Monospecific antibody as used herein is defined as a single antibody species or multiple antibody species with homogenous binding characteristics. Hybridoma cells are produced by mixing the splenic lymphocytes with an appropriate fusion partner, preferably myeloma cells, under conditions which will allow the formation of stable hybridomas. The splenic antibody producing cells and myeloma cells are fused, selected, and screened for antibody production. Hybridoma cells from antibody positive wells are cloned by a technique such as the soft agar technique of MacPherson (1973, Soft Agar Techniques, in *Tissue Culture Methods and Applications*, Kruse and Paterson, Eds, Academic Press). Monoclonal antibodies are produced in vivo by injecting respective hydridoma cells into pristine primed mice, collecting ascite fluid after an interval of time, and prepared by techniques well known in the art.

Beyond species specific monoclonal antibodies described above, the antibodies of the present invention may also be in the form of a "chimeric antibody", a monoclonal antibody constructed from the variable regions derived from say, the murine source, and constant regions derived from the intended host source (e.g., human; for a review, see Morrison and Oi, 1989, *Advances in Immunology*, 44: 65-92). The variable light and heavy genes from the rodent (e.g., mouse) antibody are cloned into a mammalian expression vector which contains an appropriate human light chain and heavy chain coding region, respectively. These heavy and light "chimeric" expression vectors are cotransfected into a recipient cell line and selected and expanded by known techniques. This cell line may then be subjected to known cell culture techniques, resulting in production of both the light and heavy chains of a chimeric antibody Such chimeric antibodies have historically been shown to have the antigen-binding capacity of the original rodent monoclonal while significantly reducing immunogenicity problems upon host administration.

A logical improvement to the chimeric antibody is the "humanized antibody," which arguably reduces the chance of the patient mounting an immune response against a therapeutic antibody when compared to use of a chimeric or full murine monoclonal antibody. The strategy of "humanizing" a murine Mab is based on replacing amino acid residues which differ from those in the human sequences by site directed mutagenesis of individual residues or by grafting of entire complementarily determining regions (Jones et al., 1986, *Nature* 321: 522-526). This technology is again now well known in the art and is represented by numerous strategies to improve on this technology; namely by implementing strategies including, but not limited to, "reshaping" (see Verhoeyen, et al., 1988, *Science* 239: 1534-1536), "hyperchimerization" (see Queen, et al., 1991, *Proc. Natl. Acad. Sci.* 88:2869-2873) or "veneering" (Mark, et al., 1994, Derivation of Therapeutically Active Humanized and Veneered anti-CD18 Antibodies Metcalf end Dalton, eds. *Cellular Adhesion: Molecular Definition to Therapeutic Potential.* New York: Plenum Press, 291-312). These strategies all involve, to some degree, sequence comparison between rodent and human sequences to determine whether specific amino acid substitutions from a rodent to human consensus is appropriate. Whatever the variations, the central theme involved in generating a humanized antibody relies on CDR grafting, where these three antigen binding sites from both the light and heavy chain are effectively removed from the rodent expressing antibody clone and subcloned (or "grafted") into an expression vector coding for the framework region of the human antibody. Therefore, a "humanized antibody" is effectively an antibody constructed with only murine CDRs (minus any additional improvements generated by incorporating one or more of the above mentioned strategies), with the remainder of the variable region and all of the constant region being derived from a human source.

Yet another improvement over re-engineered antibodies as reviewed above is the generation of fully human monoclonal antibodies. The first involves the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, fully human monoclonal antibodies This technology is again now well known in the art and is fully detailed in various publications including, but not limited to, U.S. Pat. Nos. 5,939,598; 6,075,181; 6,114,598; 6,150,584 and related family members (assigned to Abgenix, disclosing their XenoMouse technology); as well as U.S. Pat. Nos. 5,545,806; 5,569,825; 5,625,126; 5,633,425; 5,789,650; 5,877,397; 5,661,016; 5,814,318; 5,874,299; and 5,770,429 (assigned to GenPharm International and available through Medarex, under the umbrella of the "UltraMab Human Antibody Development System"). See also a review from Kellerman and Green (2002, *Curr. Opinion in Biotechnology* 13: 593-597).

Finally, techniques are available to the artisan for the selection of antibody fragments from libraries using enrichment technologies including, but not limited to, phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies which specifically bind to target cytokine. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template. Single-chain antibodies can be mono- or bispecific; bivalent or tetravalent. A nucleotide sequence encoding a single-chain antibody can be constructed using manual or automated nucleotide synthesis, cloned into an expression construct using standard recombinant DNA methods, and introduced into a cell to express the coding sequence, as described below.

The term "recombinant human antibody" represents a viable subset of "antibodies" generated by various means of recombinant DNA technology and non-human transgenics that are well known in the art. Such methodology is utilized to generate an antibody from one or the following origins: (i) a scFv or alternative antibody isolated from a combinatorial human antibody library; (ii) a partial or complete antibody generated from a respective expression vector stably or transiently transfected into a host cell, preferably a mammalian host cell; and/or (iii) an antibody isolated from a non-human transgenic animal which contains human immunoglobulin genes, or by any other known methodology which relies of the recombinant 'mixing and matching' of human immunoglobulin gene sequences to other DNA sequences in order to generate the human recombinant antibody of interest.

In a similar manner, a gene encoding a target protein disclosed herein, either in a normal or in a mutant form, can be down regulated through the use of antisense oligonucleotides directed against the gene or its transcripts. A similar strategy can be utilized as discussed herein in connection with an antibody raised against such a target protein. For a particularly valuable review of the design considerations and use of antisense oligonucleotides (see Uhlmann et al., *Chemical Reviews,* 1990, 90(4):543-584), the disclosure of which is hereby incorporated by reference. The antisense oligonucleotides of the present invention may be synthesized by any of the known chemical oligonucleotide synthesis methods. Such methods are generally described, for example, in Winnacker, *Chirurg* 1992, 63(8), Supp. 145-149 (German).

Since the complete nucleotide synthesis of DNA complementary to any of the target genes contemplated herein is known, the mRNA transcript of the cDNA sequence is also known. As such, antisense oligonucleotides hybridizable with any portion of such transcripts may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12-40 nucleotides are preferred, more preferably 15-30 nucleotides, most preferably 18-26 nucleotides. Sequences of 18-24 nucleotides are most particularly preferred.

In one embodiment, the antisense therapy may be accomplished by siRNA or shRNA treatment. SiRNAs are typically short (19-29 nucleotides), double-stranded RNA molecules that cause sequence-specific degradation of complementary target mRNA known as RNA interference (RNAi) (Bass, Nature, 2001, 411:428-429). Accordingly, in some embodiments, the siRNA molecules comprise a double-stranded structure comprising a sense strand and an antisense strand, wherein the antisense strand comprises a nucleotide sequence that is complementary to at least a portion of a desired nucleic acid sequence and the sense strand comprises a nucleotide sequence that is complementary to at least a portion of the nucleotide sequence of said antisense region, and wherein the sense strand and the antisense strand each comprise about 19-29 nucleotides.

The siRNA molecules targeted to desired sequence can be designed based on criteria well known in the art (e.g., Elbashir et al., *EMBO J.*, 2001, 20(23):6877-88). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 bp after the initiation ATG and at least 75 bp before the stop codon; and the target segment preferably should not contain more than 16-17 contiguous base pairs of homology to other coding sequences.

Based on some or all of these criteria, siRNA molecules targeted to desired sequences can be designed by one of skill in the art using the aforementioned criteria or other known criteria (e.g., Gilmore et al., 2004, *J. Drug Targeting* 12(6): 315-40; Reynolds et al., 2004, *Nature Biotechnol.* 22(3):326-30; Ui-Tei et al., 2004, *Nucleic Acids Res.* 32(3):936-948). Such criteria are available in various web-based program formats useful for designing and optimizing siRNA molecules (e.g., Sidesign Center at Dharmacon; BLOCK-IT RNAi Designer at Invitrogen; siRNA Selector at WISTAR Insitute; siRNA selection program at Whitehead Institute; siRNA Design at Integrated DNA Technologies; siRNA Target Finder at Ambion; AND siRNA Target Finder at Genscript). Accordingly, a person of skill in the art may just find suitable siRNA sequences by entering the desired template sequence into one or more of the software programs listed above.

In one embodiment, the siRNA molecules targeted may be to desired sequences can be produced in vitro by annealing two complementary single-stranded RNA molecules together (one of which matches at least a portion of a desired nucleic acid sequence) (e.g., U.S. Pat. No. 6,506,559) or through the use of a short hairpin RNA (shRNA) molecule which folds back on itself to produce the requisite double-stranded portion (Yu et al., *Proc. Natl. Acad. Sci. USA*, 2002, 99:6047-6052). Such single-stranded RNA molecules can be chemically synthesized (e.g., Elbashir et al., 2001, *Nature* 411(6836):494-8) or produced by in vitro transcription using DNA templates (e.g., Yu et al., 2002, *Proc. Natl. Acad. Sci. USA* 99:6047-6052). When chemically synthesized, chemical modifications can be introduced into the siRNA molecules to improve biological stability. Such modifications include phosphorothioate linkages, fluorine-derivatized nucleotides, deoxynucleotide overhangs, 2'-O-methylation, 2'-O-allylation, and locked nucleic acid (LNA) substitutions (Dorset and Tuschl, 2004, *Nat. Rev. Drug Discov.* 3:318); Gilmore et al., 2004, *J. Drug Targeting* 12(6):315-40).

Administration of a siRNA as a biological agent is contemplated when practicing the methods of the present invention. More specifically, siRNA molecules targeted to desired target sequences can be released from the implanted pharmaceutical depot and taken up into lymphocytes within the knee joint in order to inhibit expression of a target gene encoding an inflammatory-related cytokine, chemokine, etc. As discussed herein, a targeted inflammatory cytokine or protein related to the inflammatory response includes, but is not limited to, TNF-α, IL-1β, IL-6, IL-8, NF-κB, High Mobility Group Box 1 (HMG-B1), IL-2, and IL-15, while a specific anti-inflammatory cytokine or related protein which may promote an anti-inflammatory response includes but is not limited to IL-10, IL-4, IL-13 and TGF-β, as well as any other cytokine or pathway related protein which modulates the respective anti-inflammatory cytokine so as to impart an increase in the ability to reduce inflammation and pain within a joint such as the knee joint.

Every patent and non-patent publication cited in the instant disclosure is incorporated into the disclosure by reference to the same effect as if every publication is individually incorporated by reference.

A person skilled in the art will appreciate that various modifications of these embodiments are possible. Among these modifications are different sustained-release formulations of the anti-cytokine agent and active ingredient. Moreover, the depot is not limited to attachment within the knee joint, as disclosed above. This embodiment of the invention is intended only for illustrative purposes. Rather, the present invention contemplates a method of securing the depot to any ligament of any joint within the body that suffers from joint inflammation, trauma and/or disorder such as, but not limited to, a ligament within a shoulder joint, an elbow joint, a hip joint, or any other synovial joint within the body.

What is claimed is:

1. A method of providing prolonged treatment within a knee joint comprising securing at least one depot implant containing a biological agent exclusively to ligament tissue within the synovial space of the joint such that the at least one depot is positioned in the center of said ligament tissue, wherein the depot implant is secured so as to allow for normal joint articulation, wherein the treatment is inflammation of the joint and wherein the biological agent is selected from a group consisting of anti-inflammatory cytokines, inflammatory cytokine antagonists, anti-inflammatory agents and combinations thereof.

2. The method of claim 1 wherein the biological agent is an inflammatory cytokine antagonist and the inflammatory cytokine is selected from the group consisting of TNF-α, IL-1β, IL-6, IL-8, NF-κB, High Mobility Group Box 1 (HMG-B1), IL-2, and IL-15.

3. The method of claim 1 where the biological agent is an anti-inflammatory cytokine.

4. The method of claim 3 wherein the cytokine is selected from the group consisting of IL-10, IL-4, IL-13, and TGF-β.

5. A method of claim 1 wherein the biological agent released from the depot treats a trauma of a knee joint.

6. A method of claim 5 wherein the trauma is selected from the group consisting of a trauma to a anterior cruciate ligament, a posterior cruciate ligament, a medial collateral ligament, a lateral collateral ligament, a patellar ligament, a medial meniscus, a lateral meniscus and a chondrol fracture.

7. The method of claim 1 wherein the inflammation of the joint is caused by a disorder selected from the group consisting of osteoarthritis, chondromalacia, and rheumatoid arthritis.

8. A method of claim 1 wherein the depot is secured to the ligament selected from the group consisting of an anterior cruciate ligament and a posterior cruciate ligament.

9. A method of claim 1 wherein the depot is secured to the ligament by at least one suture.

10. A method of claim 1 wherein a plurality of depots are coupled together and secured to the ligament by at least one suture.

11. A method of claim 1 wherein the depot is secured to the ligament by a clasp.

12. A method of claim 1 wherein the depot is secured to the ligament by a barbed rod.

13. A method of claim 1 wherein the depot comprising a flexible gel is injected into the ligament and the gel polymerizes upon injection into the ligament such that polymerization secures the depot within the ligament.

14. A method of claim 1 wherein the depot is surgically secured to ligament.

15. A method of claim 1 wherein the depot is secured to the ligament utilizing a minimally invasive technique.

16. A method of treating pain and inflammation in a knee joint while reducing systemic side effects of a drug comprising: securing at least one depot implant containing an anti-inflammatory agent exclusively to the center of an anterior cruciate ligament within the synovial space of a knee joint, wherein the depot implant is secured so as to allow for normal joint articulation and limiting the delivery of the biological to knee joint.

17. A method of implanting a depot into a synovial space of a knee joint comprising:
   making at least one incision within a ligament of the joint in the center of the ligament; and
   coupling the depot containing a biological agent to the center of the ligament through the incision such that the depot may gradually release the biological agent contained therein while allowing for normal joint articulation, wherein the biological agent is selected from a group consisting of anti-inflammatory cytokines, inflammatory cytokine antagonists, anti-inflammatory agents and combinations thereof.

* * * * *